United States Patent
Jensen et al.

(10) Patent No.: US 6,306,370 B1
(45) Date of Patent: *Oct. 23, 2001

(54) COMPOSITIONS AND METHODS FOR WHITENING AND DESENSITIZING TEETH

(75) Inventors: Steven D. Jensen, Riverton; Dan E. Fischer, Sandy, both of UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/191,854

(22) Filed: Nov. 12, 1998

Related U.S. Application Data

(63) Continuation-in-part of application No. 08/866,288, filed on May 30, 1997, now Pat. No. 5,855,870, and a continuation-in-part of application No. 08/865,910, filed on May 30, 1997, now Pat. No. 5,851,512.

(51) Int. Cl.[7] ..................................................... A61K 7/16
(52) U.S. Cl. ................................. 424/49; 424/52; 424/53; 424/54; 514/944; 514/818; 433/215
(58) Field of Search ..................................... 424/49, 52, 53, 424/673, 54; 514/944, 818; 433/215

(56) References Cited

U.S. PATENT DOCUMENTS

| Re. 28,667 | 12/1975 | Gores | 128/136 |
|---|---|---|---|
| Re. 34,196 | 3/1993 | Munro | 433/215 |

(List continued on next page.)

FOREIGN PATENT DOCUMENTS

| 1 489 712 | 11/1965 | (DE) . |
|---|---|---|
| 1 566 227 | 10/1969 | (DE) . |
| 28 48 237 | 11/1978 | (DE) . |
| 0 286 766 | 10/1988 | (EP) . |
| 0 325 267 | 7/1989 | (EP) . |
| 528007 | 12/1983 | (ES) . |
| 8100383 | 8/1982 | (NL) . |

OTHER PUBLICATIONS

Albers, Harry F., *Tooth Colored Restoratives,* Ch. 6, Sep. 1985.

Amigoni et al., "The Use of Sodium Bicarbonate and Hydrogen Peroxide Periodontal Therapy: A Review", *JADA*, vol. 114, pp. 217–221 (Feb. 1987).

Archambault, Dr. Gregory A., "Home Bleaching" *Nation–Wide Dental*, vol. 2, No. 22, Jan. 1990.

Arens, Donald E. et al., "A Practical Method of Bleaching Tetracycline–Stained Teeth", *Oral Surg., Oral Med., Oral Path.* vol. 34 (No. 5), Nov. 1972.

Arzt, Alvin H. "Updating Tetracycline–Stained Teeth Bleaching Technique" *Quintessence International,* Jan. 1981, No. 1, pp. 15–18.

(List continued on next page.)

*Primary Examiner*—Raj Bawa
(74) *Attorney, Agent, or Firm*—Workman, Nydegger & Seeley

(57) ABSTRACT

Composition and methods that include potassium nitrate for whitening and/or reducing tooth sensitivity. The dental compositions may optionally include a dental bleaching agent, such as hydrogen peroxide or carbamide peroxide. The dental compositions may be applied directly to the person's teeth, or they may be loaded into a comfortable fitting, flexible, thin-walled dental tray and placed over the person's teeth. In that case, the dental compositions will include a tackifying agent, such as carboxypolymethylene, which assists the composition in retaining the dental tray over the person's teeth as a result of the adhesive properties of the dental composition rather than due to mechanical interlocking of the tray over the person's teeth. The dental compositions may further include anticariogenic and antimicrobial agents.

23 Claims, 5 Drawing Sheets

U.S. PATENT DOCUMENTS

| | | | |
|---|---|---|---|
| 165,584 | 7/1875 | Hopfen | 128/136 |
| 767,553 | 8/1904 | Edgelow | 604/77 |
| 803,474 | 10/1905 | Dennis | 433/80 |
| 803,475 | 10/1905 | Dennis | 128/136 |
| 1,371,029 | 3/1921 | Jennings | 128/136 |
| 1,642,653 | 9/1927 | Goldstein | 433/215 |
| 1,691,785 | 11/1928 | Remensnyder | 601/139 |
| 1,818,146 | 8/1931 | Maker | 128/136 |
| 1,934,688 | 11/1933 | Ackerman | 604/77 |
| 2,257,709 | 9/1941 | Anderson | 128/260 |
| 2,669,988 | 2/1954 | Carpenter | 128/136 |
| 2,798,053 | 7/1957 | Brown | 260/2.2 |
| 2,835,628 | 5/1958 | Saffir | 167/84 |
| 2,858,281 | 10/1958 | Bauman et al. | 260/2.2 |
| 2,923,692 | 2/1960 | Ackerman et al. | 260/17.4 |
| 2,985,625 | 5/1961 | Jones | 260/78 |
| 3,060,935 | 10/1962 | Riddell | 128/260 |
| 3,073,300 | 1/1963 | Berghash | 128/136 |
| 3,107,668 | 10/1963 | Thompson | 128/136 |
| 3,224,441 | 12/1965 | Monaghan | 128/136 |
| 3,224,443 | 12/1965 | Monaghan | 128/136 |
| 3,234,942 | 2/1966 | Simor | 128/172.1 |
| 3,247,844 | 4/1966 | Berghash | 128/136 |
| 3,250,272 | 5/1966 | Greenberg | 128/136 |
| 3,319,626 | 5/1967 | Lindsay | 128/136 |
| 3,339,547 | 9/1967 | Drabkowski | 128/260 |
| 3,379,193 | 4/1968 | Monaghan | 128/136 |
| 3,380,446 | 4/1968 | Martin | 128/24 |
| 3,385,291 | 5/1968 | Martin | 128/62 |
| 3,399,457 | 9/1968 | Hagman | 32/19 |
| 3,416,527 | 12/1968 | Hoef | 128/260 |
| 3,448,738 | 6/1969 | Berghash | 128/136 |
| 3,481,329 | 12/1969 | Warren, Jr. | 128/66 |
| 3,499,844 | 3/1970 | Kibbel et al. | 252/316 |
| 3,505,995 | 4/1970 | Greenberg | 128/136 |
| 3,527,218 | 9/1970 | Westine | 128/229 |
| 3,527,219 | 9/1970 | Greenberg | 128/260 |
| 3,536,069 | 10/1970 | Gores | 128/136 |
| 3,567,823 | 3/1971 | Yamaga et al. | 424/132 |
| 3,624,909 | 12/1971 | Greenberg | 32/40 |
| 3,625,215 | 12/1971 | Quisling | 128/260 |
| 3,657,413 | 4/1972 | Rosenthal | 424/81 |
| 3,688,406 | 9/1972 | Porter et al. | 32/40 |
| 3,742,942 | 7/1973 | Westline | 128/62 |
| 3,844,286 | 10/1974 | Cowen | 128/260 |
| 3,863,006 | 1/1975 | Hodosh | 424/49 |
| 3,911,104 | 10/1975 | Harrison | 424/52 |
| 3,955,281 | 5/1976 | Weitzman | 32/14 |
| 3,969,499 | 7/1976 | Lee, Jr. et al. | 424/52 |
| 3,976,223 | 8/1976 | Jass et al. | 222/94 |
| 3,988,433 | 10/1976 | Benedict | 424/53 |
| 3,998,945 | 12/1976 | Vit | 424/53 |
| 4,012,839 | 3/1977 | Hill | 32/15 |
| 4,032,627 | 6/1977 | Suchan et al. | 424/54 |
| 4,044,762 | 8/1977 | Jacobs | 128/136 |
| 4,057,621 | 11/1977 | Pashley et al. | 424/49 |
| 4,064,628 | 12/1977 | Weitzman | 32/14 |
| 4,138,814 | 2/1979 | Weitzman | 33/14 |
| 4,164,940 | 8/1979 | Quinby | 128/62 |
| 4,173,219 | 11/1979 | Lentine | 128/260 |
| 4,173,505 | 11/1979 | Jacobs | 156/285 |
| 4,239,818 | 12/1980 | LaBate | 427/236 |
| 4,244,942 | 1/1981 | Kamishita et al. | 424/81 |
| 4,251,507 | 2/1981 | Olson | 424/49 |
| 4,283,385 | 8/1981 | Dhabhar et al. | 424/52 |
| 4,302,441 | 11/1981 | Muhlemann et al. | 424/48 |
| 4,343,608 | 8/1982 | Hodosh | 433/224 |
| 4,357,318 | 11/1982 | Shah et al. | 424/52 |
| 4,376,628 | 3/1983 | Aardse | 433/80 |
| 4,400,373 | 8/1983 | Hodosh | 424/49 |
| 4,407,675 | 10/1983 | Hodosh | 106/35 |
| 4,419,992 | 12/1983 | Chorbajian | 128/136 |
| 4,428,373 | 1/1984 | Seid et al. | 604/77 |
| 4,431,631 | 2/1984 | Clipper et al. | 424/53 |
| 4,518,721 | 5/1985 | Dhabhar et al. | 523/120 |
| 4,522,805 | 6/1985 | Gordon | 424/52 |
| 4,522,806 | 6/1985 | Muhlemann et al. | 424/52 |
| 4,528,180 | 7/1985 | Schaeffer | 424/52 |
| 4,537,778 | 8/1985 | Clipper et al. | 424/53 |
| 4,544,354 | 10/1985 | Gores et al. | 433/42 |
| 4,557,692 | 12/1985 | Chorbajian | 433/215 |
| 4,560,351 | 12/1985 | Osborne | 433/80 |
| 4,568,536 | 2/1986 | Kronenthal et al. | 424/22 |
| 4,592,487 | 6/1986 | Simon et al. | 222/94 |
| 4,592,488 | 6/1986 | Simon et al. | 222/94 |
| 4,631,185 | 12/1986 | Kim | 424/49 |
| 4,645,662 | 2/1987 | Nakashima et al. | 424/52 |
| 4,661,070 | 4/1987 | Friedman | 433/203.1 |
| 4,687,663 | 8/1987 | Schaeffer | 424/52 |
| 4,696,757 | 9/1987 | Blank et al. | 252/186.29 |
| 4,751,072 | 6/1988 | Kim | 424/49 |
| 4,755,386 | 7/1988 | Hsiao et al. | 424/435 |
| 4,770,634 | 9/1988 | Pellico | 433/217 |
| 4,788,052 | 11/1988 | Ng et al. | 424/53 |
| 4,812,308 | 3/1989 | Winston et al. | 424/52 |
| 4,839,156 | 6/1989 | Ng et al. | 424/53 |
| 4,839,157 | 6/1989 | Mei-King Ng et al. | 424/53 |
| 4,849,213 | 7/1989 | Schaeffer | 424/53 |
| 4,895,721 | 1/1990 | Drucker | 424/53 |
| 4,902,227 | 2/1990 | Smith | 433/215 |
| 4,939,284 | 7/1990 | Degenhardt | 558/142 |
| 4,954,487 | 9/1990 | Cooper et al. | 514/159 |
| 4,966,777 | 10/1990 | Gaffab et al. | 424/52 |
| 4,968,251 | 11/1990 | Darnell | 433/216 |
| 4,971,782 | 11/1990 | Rudy et al. | 424/53 |
| 4,980,152 | 12/1990 | Frazier et al. | 424/52 |
| 4,983,379 | 1/1991 | Schaeffer | 424/52 |
| 4,983,381 | 1/1991 | Torres Zaragoza | 424/53 |
| 4,988,500 | 1/1991 | Hunter et al. | 424/53 |
| 4,990,089 | 2/1991 | Munro | 433/215 |
| 4,992,258 | 2/1991 | Mason | 424/49 |
| 5,015,466 | 5/1991 | Parran, Jr. et al. | 424/52 |
| 5,098,303 | 3/1992 | Fischer | 433/215 |
| 5,122,365 | 6/1992 | Murayama | 424/49 |
| 5,153,006 | 10/1992 | Hodosh | 424/718 |
| 5,182,099 | 1/1993 | Jönsson et al. | 424/49 |
| 5,188,822 | 2/1993 | Viccaro et al. | 424/52 |
| 5,234,342 | 8/1993 | Fischer | 433/215 |
| 5,240,697 | 8/1993 | Norfleet et al. | 424/52 |
| 5,256,402 | 10/1993 | Prencipe et al. | 424/53 |
| 5,352,439 | 10/1994 | Norfleet et al. | 424/52 |
| 5,374,417 | 12/1994 | Norfleet et al. | 424/49 |
| 5,376,006 | * 12/1994 | Fischer | 424/53 |
| 5,401,495 | 3/1995 | Murayama | 424/49 |
| 5,403,577 | 4/1995 | Friedman | 424/45 |
| 5,409,631 | * 4/1995 | Fischer | 424/53 |
| 5,427,768 | 6/1995 | Tung | 424/52 |
| 5,437,858 | 8/1995 | Hungerbach et al. | 424/53 |
| 5,449,509 | 9/1995 | Jackson et al. | 424/49 |
| 5,505,933 | 4/1996 | Norfleet et al. | 424/52 |
| 5,522,726 | 6/1996 | Hodosh | 433/215 |
| 5,565,190 | 10/1996 | Santalucia et al. | 424/53 |
| 5,571,501 | 11/1996 | Toy | 424/49 |
| 5,599,527 | 2/1997 | Hsu et al. | 424/52 |
| 5,614,174 | 3/1997 | Hsu et al. | 424/49 |
| 5,630,999 | 5/1997 | Burke et al. | 424/49 |
| 5,631,000 | 5/1997 | Pellico et al. | 424/53 |
| 5,648,064 | 7/1997 | Gaffar et al. | 424/53 |
| 5,698,182 | 12/1997 | Prencipe et al. | 424/53 |
| 5,725,843 | * 3/1998 | Fischer | 424/49 |
| 5,746,598 | * 5/1998 | Fischer | 424/53 |

| | | | |
|---|---|---|---|
| 5,770,182 | * | 6/1998 | Fischer ................................... 424/49 |
| 6,099,868 | | 8/2000 | Hodosh ............................... 424/600 |

OTHER PUBLICATIONS

Attin et al., "Die Bleichbehandlung—ein fester Bestandteil ästhetischer Zahnheilkunde," Universitätsklinik für Abt. Poliklinik, Hugstetter Str. 55, 79106 Freiburg—Attin et al., "Bleaching—An Essential Part of Esthetic Dentistry," University Clinic for Dentistry, Oral Medicine and Orthodontics, Polyclinic, Hugstetter Str. 55, D79106, Freiburg, 1995.

BF Goodrich Chemical (Deutschland) GmbH: Carbopol®, Wasserlösliche Polymere—Carbopol®, Water Soluble Polymer, 1984.

Baumgartner, J. Craig et al., "Human Pulpal Reaction to the Modified McInnes Bleaching Technique", *Journal of Endodontics*, vol. 9, No. 12, Dec. 1983, pp. 527–529.

Bayless, J. Mark et al., "Diagnosis and Treatment of Acute Fluoride Toxicity", *JADA*, vol. 110, Feb. 1985, pp. 209–211.

Blaine, Edward et al., "Oral Hygeine Supplement for Handicapped Children," *The Journal of Dental Practice*, pp. 29–31 (May 1971).

Bouschor, Charles F., "Bleaching Fluorosis Stained Teeth", *New Mexico Dental Journal*, vol. 16, No. 1, May 1965, pp. 33–34.

Bowles, William H. et al., "Pulp Chamber Penetration by Hydrogen Peroxide Following Vital Bleaching Procedures" *Journal of Endodontics*, vol. 13, No. 8, Aug. 1987, pp. 375–377.

Budaveri, S. et al., "The Merck Index," Merck & Co., Inc., pp. 323, 1449 and 1450 (1989).

Budaveri, S. et al., "The Merck Index," Merck & Co., Inc., pp. 1521, 1536, 1537, MISC–3 and 4, CI–337 (1989).

Buffalo Dental Mfg. Co. Technical Manual for Sta–Vac mini–lab vacuum adapter; Brochure No. 895/01.

Christensen, Gordon J. et al., "Bleaching Vital Tetracycline Stained Teeth", *Quintessence International*, vol. 9, No. 6, Jun. 1978.

Cobe, Herbert J. et al, "Urea Peroxide . . . in Glycerine", *Pennsylvania Dental Journal*, vol. 25, No. 4, pp. 12–18 (Jan. 1959).

Cohen, Stephen, "A Simplified Method for Bleaching Discolored Teeth," *Digest*, pp. 303–303 (Jul. 1968).

Cohen et al., "Bleaching Tetracycline–Stained Vital Teeth", *Oral Surgery*, vol. 29, No. 3, pp. 465–471 (Mar. 1970).

Cohen, Steven et al. "Human Pulpal Response to Bleaching Procedures on Vital Teeth", *Journal of Endodontics*, vol. 5, No. 5, May 1979, pp. 134–138.

Colon, P.G. Jr., "Removing Fluorosis Stains From Teeth", *Quintessence International*, vol. 2, No. 6, p. 1.

Compton, Duane E., "Bleaching of Tetracycline–Stained Vital Teeth", *Journal of Endodontics*, vol. 5, No. 4, May 1979.

Corcoran, John F. et al., "Bleaching of Vital Tetracycline Stained Teeth", *Journal of the Michigan Dental Association*, vol. 56, No. 12, Dec. 1974, pp. 340–343.

Croll, Theodore P. et al., "Enamel Color Modification By Controlled Hydrochloric Acid–Pumice Abrasion. I. Technique and Examples" *Quintessence International*, vol. 17, No. 2, 1986.

Croll, Theodore P. et al, "Enamel Color Modification By Controlled Hydrochloric Acid–Pumice Abrasion. II. Further Examples" *Quintessence International*, vol. 17, No. 3, 1986.

Croll, Theodore P. et al., "A Case of Enamel Color Modification: 60 Year Results" *Quintessence International* vol. 18, No. 7, 1987, pp. 493–495.

Cvek, Miomir et al, "External Root Resorption Following Bleaching of Pulpless Teeth With Oxygen Peroxide", *Endod. Dent. Traumatol*, 1985 vol. 1, pp. 56–60.

Darnell, Daniel H. et al., "Vital Tooth Bleaching: The White & Brite Technique," *Compend. Cont. Educ. Dent.*, vol. XI, No. 2, pp. 1–2 (undated).

Davies, A.K. et al., "Photo–oxidation of Tetracycline Absorbed on Hydroxyapatite in Relation to the Light–Induced Staining of Teeth", *Material Science*, vol. 64, No. 6, p. 936–939.

*Dental Pharmacology*, pp. 296–297 (Mar. 21, 1990).

Dickstein, Benjamin, "Neonatal Oral Candidiasis: Evaluation of a New Chemotherapeutic Agent," *Clinical Pediatrics*, pp. 485–488 (Aug. 1964).

Dietz, Ellen Roberta, "Bleaching Vital Teeth", *The Dental Assistant*, Jan./Feb. 1988, pp. 7–8.

Drew, Claudine Paula, "Teeth Bleaching . . . A Vital Technique For You To Know", *Dental Assisting*, Sep./Oct. 1988, pp. 23–25.

Ekstrand, Jan et al., "Systemic Fluoride Absorption Following Fluoride Gel Application," *J. Dent. Res.*, vol. 59, No. 6, p. 1067 (Jun. 1980).

Englander, H.R. et al., "The Prevention of Dental Caries in the Syrian Hamster after Repeated Topical Application of Sodium Fluoride Gels", *JADA*, vol. 73, pp. 1342–1347 (Dec. (1966).

Englander et al., "Clinical Anticaries Effect of Repeated Topical Sodium Fluoride Applications by Mouthpieces", *JADA*, vol. 75, pp. 638–644 (Sep. 1967).

Fasanaro, Tom S., *Bleaching Teeth: History, Chemicals, and Methods Used For Common Tooth Discolorations*, (Jan. 1991, 2nd Ed.).

Feiglin, Barry, "A 6–year Recall Study of Clinically Chemically Bleached Teeth," *Oral Surg. Oral Med. Oral Pathol*, vol. 63, pp. 610–613 (May 1987).

Feinman, Ronald A., "A Combination Theapy" *CDA Journal*, Apr. 1987, pp. 10–13.

Feinman et al., "Chemical, Optical, and Physiologic Mechanisms of Bleaching Products: A Review," *The Bleaching Report*, vol. 3, pp. 32–37, 1991.

Feinman, Ronald A., "Matrix Vital Bleaching: A Review" *Esthetic Dentistry Update*, vol. 2, No. 3, Jun. 1991, pp. 42–27.

Feinman, Ronald A., "History of Bleaching Nonvital Teeth" *Bleaching: A New Addition to the Esthetic Dentistry Armamentarium*, 1990, pp. 11–12.

Fields, John P. "Intracoronal Bleaching of Tetracycline–Stained Teeth: A Case Report" *Journal of Endodontics*, vol. 8, No. 11, Nov. 1982, pp. 512–513.

Firestone, A.R. et al., "Effect of Topical Application of Urea Peroxide on Caries Incidence and Plaque Accumulation in Rats," *Caries Res.*, vol. 16, pp. 112–117 (1982).

Fogel, Maxwell S., et al., "Use of an Antiseptic Agent in Orthodontic Hygiene," *Dental Survey*, pp. 50–54 (Oct. 1971).

Franchi, Gene J., "A Practical Technique for Bleaching Discolored Crowns of Young Permanent Incisors," *Journal of Dentistry for Children*, pp. 68–70 (undated).

Freedman, George A., "The Safety of Tooth Whitening," *Dentistry Today*, pp. 32–35 (Apr. 1990).

Friedman et al., "Incidence of External Root Resorption and Esthetic Results in 58 Bleached Pulpless Teeth," *Endod. Dent. Traumatol,* pp. 23–26 (Jun. 1987).

Gallion et al., "Vital Bleaching, Effects on Brightness", Alumni Dental Convention, Loma Linda University School of Dentistry (1990).

Genesis 2000 advertisement for "Genesis White" whitening system (Mar. 21, 1990).

Gertenrich et al., "Treatment of Dilantin Gingival Hyperplasia with Proxigel," *American Journal of Mental Deficiency,* vol. 78, No. 4, pp. 502–504 (1974).

Goldstein, Ronald E., "Bleaching Teeth: New Materials—New Role", *JADA,* Special Issue, Dec. 1987, pp. 44–52.

Grogan, David Francis, "Agents Used in Bleaching Teeth", *Tufts Dental Outlook,* vol. 20, No. 1, Mar., 1946, pp. 20–23.

Hardman, Patrick K. et al., "Stability of Hydrogen Peroxide As a Bleaching Agent", *General Dentistry,* Mar./Apr. 1985, pp. 121–122.

Harrington, Gerald W. et al, "External Resorption associated with bleaching of pulpless teeth", *Journal of Endodontics,* vol. 5, No. 11, Nov. 1979 pp. 344–348.

Haywood, Van B. et al., "Nightguard Vital Bleaching", *Quintessence International,* vol. 20, No. 3, pp. 173–176 (1989).

Haywood, Van B., "Letter to the Editor", *Quintessence International,* vol. 20, No. 10, (1989), pp. 697.

Haywood, Van B., "Nightguard Vital Bleaching: Effects on Enamel Surface Texture and Diffusion", *Quintessence International,* vol. 21, No. 10, (1990), pp. 801–804.

Haywood, Van B., "Nightguard Vital Bleaching: A History and Products Update: Part 1," *Esthetic Dentistry Update,* vol. 2, No. 4, Aug. 1991, pp. 63–66.

Heller, L., "Is Yor Dentist Up–To–Date?", *Redbook,* pp. 20–26, at 26 (Mar. 1990).

Horii, A.A., et al., "A Vital Applicator for Assessing Drugs in the Treatment of Caries and Periodontal Disease in the Hamster," Laboratory of Histology and Pathology, National Institute of Dental Research, National Institutes of Health, Departmen of Health, Education, and Welfare, U.S. Public Health Service, Bethesda Maryland, p. 152 (submitted for publication Aug. 19, 1963).

Jordan, Ronald E., et al., "Conservative Vital Bleaching Treatment of Discolored Dentition", *Compendium,* vol. V, No. 10, Nov./Dec. 1984, pp. 803–808.

Jordan, Ronald E., et al., "Conservative Applications of Acid Etch–Resin Techniques", *Dental Clinics of North America,* vol. 25, No. 2, Apr. 1981, pp. 307–337.

Kaslick, Ralph S., "Studies on the Effects of Urea Peroxide Gel on Plaque Formation and Gingivitis," *J. Periodontol.,* pp. 230–232 (Apr. 1975).

Kehoe, Joseph C., "Bleaching Today", *Florida Dental Journal,* vol. 55, No. 1, Spring 1984, pp. 12–15.

Kennedy, Nathaniel, "The Tetracycline Dilemma and a Vital Bleaching Technique", *CDS Review,* vol. 69, No. 5, May 1976, pp. 28–30.

Kesling, Harold D., "The Tooth Positioner as the Means of Final Positioning of Teeth to a Predetermined Pattern," *Journal of Dentistry for Children,* pp. 103–105.

Kirkegaard et al., "Children's Response to Various Local Fluoride Treatments", *Acute Odontol. Scand.,* vol. 38, No. 4, pp. 235–240 (1980).

Kundergren et al,. "In Vivo and In Vitro Studies on a New Peroxide–Containing Toothpaste", *Scand. J. Dent. Res.,* vol. 81, pp. 544–547 (1973).

LeCompte, E.J. et al., "Oral Fluoride Retention Following Various Topical Application Techniques in Children," *J. Dent. Res.,* vol. 61, No. 12, pp. 1397–1400 (1982).

Ledoux, William R., et al., "Structural Effects of Bleaching On Tetracycline–Stained Vital Rat Teeth", *The Journal of Prosthetic Dentistry,* Jul. 1985, vol. 54, No. 1, pp. 55–59.

Lowney, Jeremiah J., "A Simplified Technique for Bleaching a Discolored Tooth," *Dental Digest,* pp. 446–448, (Oct. 1964).

McEvoy, S., "Chemical Agents for Removing Intrinsic Stains from Vital Teeth. I. Technique Development", *Quintessence International,* vol. 20, No. 5, pp. 323–328 (1989).

McEvoy, S., "Chemical Agents for Removing Intrinsic Stains from Vital Teeth. II. Current Techniques and their Clinical Application", *Quintessence International,* vol. 20, No. 6, pp. 379–384 (1989).

McMurray, Crawford A., "Removal of Stains From Mottled Enamel Teeth", *Texas Dental Journal,* vol. 59, No. 9, Sep. 1941.

Mello, Hilton S., "The Mechanism of Tetracycline Staining in Primary and Permanent Teeth", *Dentistry for Children,* vol. 34, No. 6, pp. 478–487.

Merwe, P.K. v.d., "The Removal Of the Stain From Mottled Teeth", *The South African Dental Journal,* vol. 18, No. 2, Feb. 1944, pp. 31–34.

Morrison, Scott W., "Vital Tooth Bleaching—The Patient's Viewpoint", *General Dentistry,* May–Jun. 1986, pp. 238–240.

Murrin, James R., et al., "Chemical Treatment of Vital Teeth With Intrinsic Stain", *ODJ,* Nov. 1982, pp. 6–10.

Myers, Malcolm, et al., "Effect of Daily Application of Fluoride in a Custom Fitted Mouthpiece on Plaque Flora Associated with Dental Decay", *Journal of Dental Research,* vol. 50, No. 3, pp. 597–599 (May 1971).

Nathanson, Dan et al., "Bleaching Vital Teeth: A Review and Clinical Study" *Compend Contin. Educ. Dent.,* vol. VIII, No. 7, pp. 490–498.

Newbrun, E., "Topical Fluoride Therapy: Discussion of Some Aspects of Toxicology, Safety, and Efficacy," *J. Dent. Res.,* vol. 66, No. 5, pp. 1084–1086 (1987).

Nutting, Edwin B., et al., "Chemical Bleaching of Discolored Endodontically Treated Teeth", *Dental Clinics of North America,* Nov., 1967, pp. 655–662.

Prinz, Herman, "Recent Improvements in Tooth Bleaching", *The Dental Cosmos,* vol. 66, pp. 558–560 (May 1924).

Reddy, J. et al., "The Effect of a Urea Peroxide Rinse on Dental Plaque and Gingivitis," *J. Periodontol.,* pp. 607–610 (Oct. 1976).

Rees, Terry D. et al., "Oral Ulcerations with Use of Hydrogen Peroxide," *J. Periodontol.,* pp. 689–692 (1986).

Reid, J.S. et al. "A Suggested Method of Bleaching Tetracycline–Stained Vital Teeth", *British Dental Journal,* vol. 142, No. 8, Apr. 1977, p. 261.

Reid, J.S. "Patient Assessment of The Value of Bleaching Tetracycline–Stained Teeth", *Journal of Dentistry for Children,* Sep./Oct. 1985, pp. 353–355.

Rethman, Jill, "At–Home Tooth Bleaching: A Review for the Dental Professional," *J. Practical Hygiene,* pp. 1–5, (May/Jun. 1994).

Richardson, Sue Ellen, "Home Bleaching: Effectiveness, History, Technique, Bleaches, Cost and Safety," *J. Greater Houston Dent. Soc.,* pp. 22–25 (Nov. 1989).

Ripa, Louis W. et al., "Effect of Prior Toothcleaning on Biannual Professional APF Topical Fluoride Gel–tray Treatments", *Clinical Preventative Dentistry*, vol. 5, No. 4, Jul.–Aug. 1983.

Ripa, Louis W. et al., "Effect of Prior Toothcleaning on Biannual Professional Acidulated Phosphate Fluoride Topical Fluoride Gel–tray Treatments—Results After Three Years", *Caries Res.* 18:457–464 (1984).

Seale, N.S. et al., "Systematic Assessment of Color Removal Following Vital Bleaching of Intrinsically Stained Teeth," *J. Dent. Res.*, vol. 64, No. 3, pp. 457–461 (1985).

Shapiro, William B., et al., "The Influence of Urea Peroxide Gel on Plaque, Calculus and Chronic Gingival Inflammation," *J. Periodontology*, pp. 636–639 (Oct. 1973).

Shipman, B., et al., "The Effect of a Urea Peroxide Gel on Plaque Deposits and Gingival Status,"*J. Periodont.*, pp. 283–285 (1971).

Simon, James F. et al., "Efficacy of Vital Home Bleaching," *CDA Journal*, (Jan. 1993).

Smith et al., "Further Studies on Methods of Removing Brown Stain from Mottled Teeth", *JADA*, vol. 29, p. 571–576 (Apr. 1942).

Spasser, Herbert F. "A Simple Bleaching Technique Using Sodium Perborate", *New York State Dental Journal*, No. 27, Aug.–Sep. 1961, pp. 332–334.

Spencer, Duane E., "A Conservative Method of Treating Tetracycline Stained Teeth", *ASBC Journal of Dentistry For Children*, vol. 29, No. 6, Nov./Dec. 1972, pp. 25–28.

Stewart, George G. et al., "A Study of a New Medicament in the Chemomechanical Preparation of Inflected Root Canals," *The Journal of the American Dental Association*, vol. 63, pp. 33–37 (Jul. 1961).

Stindt, Diana J. et al., "An Overview of Gly–Oxide Liquid in Control and Prevention of Dental Disease," *Compend Contin. Educ. Dent.*, vol. X, No. 9, pp. 514–519.

Swift, Edward J. Jr., "A Method For Bleaching Discolored Vital Teeth", *Quintessence International*, vol. 19, No. 9, 1988, pp. 607–612.

Tartakow et al., "Urea Peroxide Solution in the Treatment of Gingivitis in Orthodontics," *Am. J. Orthod.*, vol. 73, No. 5, pp. 560–567 (May 1978).

Tassman, Gusstav et al., "Hygiene in Problem Patients," *Dental Surgery*, pp. 35–42 (Feb. 1963).

Trask, P., "Orthodontic Positioner Used for Home Fluoride Treatments", *American Journal of Orthodontics*, vol. 67, No. 6, pp. 677–682 (Jun. 1975).

Tyldesley, W.R., "Acidic Stain Removers: A Short Report", *Dental Practictioner & Dental Record*, vol. 20, No. 9, May 1970 pp. 311–313.

Ward, Marcus L., "The American Textbook of Operative Dentistry," pp. 491–497 (1990).

Warren, K., "Bleaching Discolored Endodontically Treated Teeth" *Restorative Dent.*, vol. 1, No. 5, Jul. 1985.

Wayman, Blake E. et al., "Vital Bleaching Technique For Treatment of Endemic Fluorosis", *General Dentistry*, Sep.–Oct. 1981, pp. 424–427.

Weisz, W.S., "Reduction of Dental Caries through the Use of a Sodium Fluoride Mouthwash," *The Journal of the American Dental Association*, pp. 454–455, vol. 60 (Apr. 1960).

Yarborough, David K., "Tooth Bleaching Safety and Efficacy—A Review of the Literature 1988–1990," pp. 1–16.

Younger, Harold B., "Bleaching Mottled Enamel", *Texas Dental Journal*, vol. 60, No. 12, Dec. 1942, pp. 467–469.

Zillich, Richard M., "Bleaching Tetracycline Stains," *The Compendium of Continuing Education*, vol. V, No. 6 p. 465–470 (Jun. 1984).

"A New Look For Your Smile", *JADA Guide To Dental Health*, Special Issue, 1987, pp. 55–59.

Adept Report, Vol. 2, No. 1 (Winter 1991) entitled "Lightening Natural Teeth".

Den–Mat Corporation advertisement for "Rembrant Lighten Bleaching Gel" in *Dental Products Report*, p. 97 (Feb. 1990).

*Lexikon der dentalen Technologie—Dental Technology Dictionary*, Quintessenz Verlags—GmbH, pp. 274, 275, 350, 351 (1986).

Hackh's Chemical Dictionary 440 (4th Ed. 1969).

M & M Innovations advertisement for "Nu–Smile " dental bleaching system originally appearing in *Dental Products Report* (Nov. 1989).

"Die Wichtmetalle in der Zahntechnik," *Grundwissen für Zahntechniker Werkstoffkunde*, Band II, Ceasar/Ernst (Erste Auflage)—"Non Metals in Dental Technology," *Basic Sciences for Dental Technicians, Materials Science*, vol. II, Ceasar/Ernst (1st ed.).

Omnii International Advertisement for White & Brite (Mar. 21, 1990).

Omnii International Advertisement for Fluorides, etc. (Mar. 21, 1990).

Physician's Desk Reference, 1168, 1584 published by Medical Economics Co., Inc., Oracle No., NJ., (38th Ed. 1984).

Product Insert, for Peroxygel® Oral Antiseptic & Cleanser, Lot No. 55008, Product Code NDC 0021–0150–12, Product Insert No. 421220044.

Remington's Pharmaceutical Sciences, 1256, Mack Publishing, Philadelphia, PA (16th Ed. 1980).

Research on Whitening Teeth Makes News, *The North Carolina Dental Review* vol. 7, No. 2, Fall 1990.

T & S Dental and Plastics Co., Inc. "Instruction Manual for the Machine Precision Vacuum Adapter," pp. 1–20 (Mar. 21, 1990).

"The Third Stage of Comprehensive Treatment: Finishing", p. 451 (1986).

"Tooth Bleaching, Home Use Products," Clinical Research Associates Newsletter, vol. 13, Issue 7, (Jul. 1989).

"Tooth Bleaching, Home–Use Products," Clinical Research Associates Newsletter, vol. 13, Issue 12, (Dec. 1989).

Deposition of Dr. Thomas Marvin Austin with Exhibits, Civil Action No. 91–1406 WJR (Sx) (C.D. Cal.) (Aug. 1991).

Declaration of P. Michael Clinard, Civil Action No. 91–1406 WJR (Sx) (C.D. Cal.) (Jul. 1991).

Deposition (Group) of Coastal Dental Study Club, Civil Action No. 91–1406 WJR (Sx) (C.D. Cal.) (Sep. 1991).

Declaration of Dr. David H. Freshwater (2), Civil Action No. 91–1406 WJR (Sx) (C.D. Cal.) (Jul. 1991).

Deposition of Dr. David H. Freshwater with Exhibits, Civil Action No. 91–1406 WJR (Sx) (C.D. Cal.) (Sep. 1991).

Deposition of Dr. Van B. Hollywood with Exhibits, Civil Action No. 91–1406 WJR (Sx) (C.D. Cal.) (Sep. 1991).

Declaration of Dr. William W. Klusmeier (2), Civil Action No. 91–1406 WJR (Sx) (C.D. Cal.) (Apr. 1991).

Deposition of Dr. William Walter Klusmeier, Jr. with Exhibits, Civil Action No.1 91–1406 WJR (Sx) (C.D. Cal.) (Apr. 1991).

Deposition of Dan Parker with Exhibits, Civil Action No. 91–1406 WJR (Sx) (C.D. Cal.) (Aug. 1991).

Declaration of Paula Rains, Civil Action No. 91–1406 WJR (Sx) (C.D. Cal.) (May 1991).

Declaration of Dr. Phil S. Sanders, Civil Action No. 91–1406 WJR (Sx) (C.D. Cal.) (Jul. 1991).

Deposition of Dr. Phil S. Sanders with Exhibits, Civil Action No. 91–1406 WJR (Sx) (C.D. Cal.) (Jul. 1991).

Declaration of Dr. Jerry Wagner, Civil Action No. 91–1406 WJR (Sx) (C.D. Cal.) (May 1991).

Deposition of Dr. Jerry Wagner, Civil Action No. 91–1406 WJR (Sx) (C.D. Cal.) (May 1991).

Deposition of Harry F. Albers, Civil Action No. 2:95CV 0163 WJR (D. Utah) (Feb. 1996).

Deposition of Dr. Van B. Haywood, Civil Action No. 2:95CV 0163 WJR (D. Utah) (Jan. 1996).

Expert Report of Dr., Van B. Haywood, Civil Action No. 2:95CV 0163 WJR (D. Utah) (Jan. 1996).

Trial Testimony of Harry F. Albers (Direct), Civil Action No. 2:95CV 0163 WJR (D. Utah) (May 1996).

Trial Testimony of Dan E. Fischer (Direct and Rebuttal), Civil Action No. 2:95CV 0163 WJR (D. Utah) (May 1996).

Trial Testimony of Roger Hicks (Rebuttal), Civil Action No. 2:95CV 0163 (D. Utah) (May 1996).

Trial Testimony of Bryan D. Tarr (Direct), Civil Action No. 2:95CV 0163 (D. Utah) (May 1996).

Trial Testimony of Garold S. Yost (Rebuttal), Civil Action No. 2:95CV 0163 WJR (D. Utah) (May 1996).

Trial Testimony of Wayne Smith Gundry (Direct), Civil Action No. 2:95CV 0163 WJR (D. Utah) (May 1996).

Trial Testimony of Walter O. Dixon (Direct), Civil Action No. 2:95 0163 WJR (D. Utah) (May 1996).

Trial Exhibits, Civil Action No. 2:95CV 0163 WJR (D. Utah) (May 1996).

Deposition of Dr. Anthony H.L. Tjan with Exhibits, Civil Action No. 2:95CV 0163 WJR (D. Utah) (Jan. 1996).

Deposition of Dr. James R. Dunn with Exhibits, Civil Action No. 2:95CV 0163 WJR (D. Utah) (Jan. 1996).

* cited by examiner

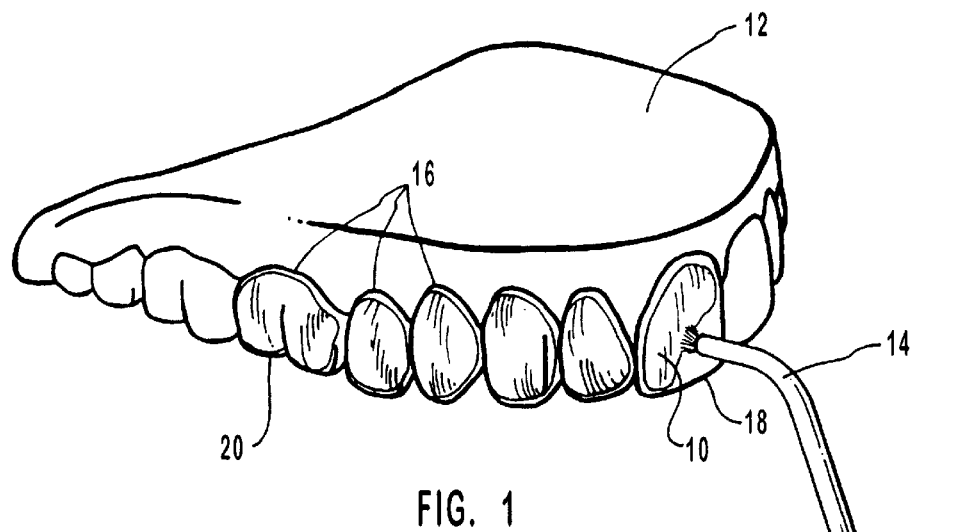
FIG. 1
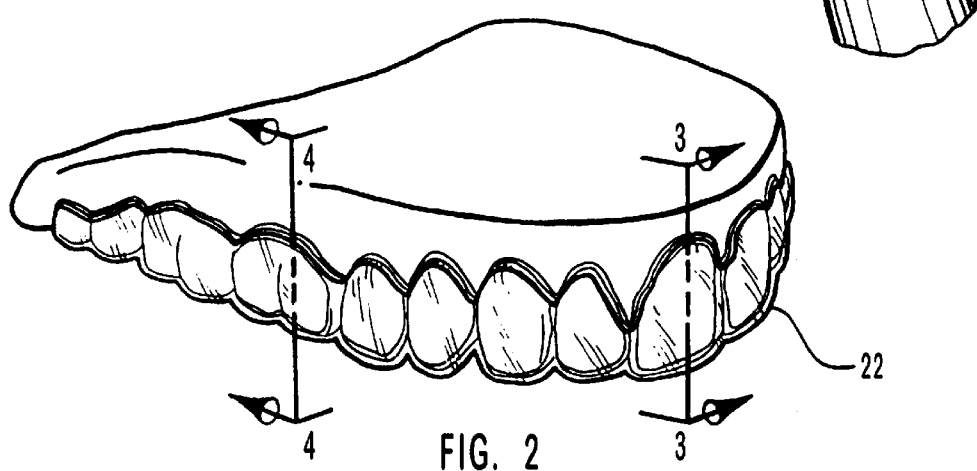
FIG. 2
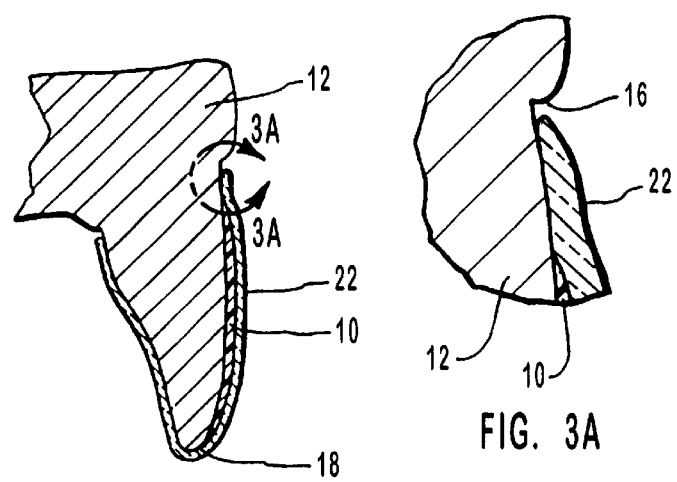
FIG. 3
FIG. 3A

COMPOSITIONS AND METHODS FOR WHITENING AND DESENSITIZING TEETH

RELATED APPLICATION

This application is a continuation-in-part of U.S. application Ser. No. 08/866,288, filed May 30, 1997, and now issued U.S. Pat. No. 5,855,870; and also CIP of U.S. application Ser. No. 08/865,910, filed May 30, 1997, now issued U.S. Pat. No. 5,851,512. For purposes of disclosing the present invention, the foregoing applications and patents are incorporated herein by specific reference.

BACKGROUND

1. The Field of the Invention

The present invention relates to compositions and methods for whitening and desensitizing teeth. The present invention relates to compositions that may be applied directly to a person's teeth for shorter periods of time, and those specifically formulated for use with flexible, thin-walled dental trays in order to provide prolonged treatment of a patient's teeth over longer periods of time.

2. The Relevant Technology

The use of certain foods and tobacco, the process of aging, diseases, trauma, medications, some congenital conditions, and environmental effects can cause teeth to become discolored. Because teeth without discolorations are usually considered to be aesthetically superior to stained or discolored teeth, there has been a heightened level of interest of late in developing compositions and methods for bleaching teeth.

A tooth is comprised of an inner dentin layer and an outer hard enamel layer that is slightly porous. The outer layer is the protective layer of the tooth. The natural color of the tooth is opaque to translucent white or slightly off-white.

Some dental compositions like dentrifices, toothpastes, gels, and powders contain active oxygen or hydrogen peroxide liberating bleaching agents. Such bleaching agents include peroxides, percarbonates and perborates of the alkali and alkaline earth metals or complex compounds containing hydrogen peroxide. Also, peroxide salts of the alkali or alkaline earth metals are known to be useful in whitening teeth.

The most commonly used dental bleaching agent is carbamide peroxide $(CO(NH_2)_2 \cdot H_2O_2)$, also called urea hydrogen peroxide, hydrogen peroxide carbamide, and perhydrolurea. Carbamide peroxide has been used by dental clinicians for several decades as an oral antiseptic. Tooth bleaching was an observed side effect of extended contact time. Over-the-counter compositions of 10% carbamide peroxide are available as GCIY-OXIDE® by Marion Laboratories and PROXIGEL® by Reed and Canuick. A bleaching gel which is able to hold a comfortable-fitting dental tray in position for an extended time period is available under the trademark OPALESCENCE® from Ultradent Products, Inc. in South Jordan, Utah. Other bleaching agents such as peroxyacetic acid $(CH_3C=OO-OH)$ and sodium perborate, are also known in the medical, dental and cosmetic arts.

Patients who have desired to have their teeth whitened have typically done so by applying a bleaching composition to the teeth by means of a dental tray for repeated treatments, or they have had to submit to conventional in-office bleaching techniques that required from 4 to 10 visits to the dental office before clinically significant results were achieved. Clinically significant results are quantifiable such as by measuring gray scale, L*, and as to yellowness or blueness, b*, in the CIE® system of color measurement or by equivalent methods.

Patients expecting their teeth to be whitened by such bleaching treatments may be pleased to have their stains removed, however, a more ideal aesthetic objective of whiter teeth may still not be adequately achieved. The removal of stains and discolorations sometimes reveal that the stains camouflaged teeth which are excessively translucent. Depending on the degree of translucency, the teeth may be revealed to be overly grey or even have portions which appear to be more transparent than is desired.

Brushing teeth with toothpaste does not address the problem of excessively translucent teeth. Brushing teeth with toothpastes or polishes is also less effective for whitening teeth compared to the application of bleaching treatments. Tooth brushing is less effective for whitening teeth as brushing teeth only cleans the external surface of the teeth while bleaching addresses internal stains in the teeth.

From the foregoing, it will be appreciated that what is needed in the art are compositions and methods for opacifying and decreasing the transparency of teeth.

It will also be appreciated that what is also needed are methods and compositions for opacifying teeth and whitening teeth without causing teeth to become overly sensitized.

What are also need are compositions and methods which are able to bleach teeth while concurrently offsetting the tendency of bleaching agents to cause teeth to become overly sensitive.

BRIEF SUMMARY AND OBJECTS OF THE INVENTION

The present invention generally relates to dental whitening compositions and methods for treating excessively translucent teeth. In addition, the present invention relates to bleaching compositions that result in reduced sensitivity. The present invention utilizes potassium nitrate $(KNO_3)$ dispersed within a carrier as an opacifying agent to reduce the tendency of some teeth to appear grey or translucent. Potassium nitrate can act as an opacifying agent either alone or in combination with a bleaching agent. Because potassium nitrate also has desensitizing or anesthetic properties, it can desensitize and/or opacify when used in conjunction with a bleaching agent, or it can be applied separately to desensitize teeth after bleaching has occurred.

In addition to potassium nitrate, other dental agents may be dispersed in the carrier. In one embodiment, the whitening compositions will include a bleaching agent such as carbamide peroxide, which can also act as a disinfectant. Alternatively or in addition to including a bleaching agent, the whitening compositions may include one or more other dental agents, such as anticariogenic agents for reinforcing teeth against tooth decay or antimicrobial agents for treating gum diseases. The most commonly used anticariogenic agents include fluoride salts, such as stannous or sodium fluoride, which can also impart antidemineralization or even remineralization properties to the tooth whitening compositions. Examples of preferred antimicrobial agents include chlorohexidine, tetracycline, cetyl pyridinium chloride, benzalkonium chloride, cetyl pyridinium bromide, methyl benzoate, and propyl benzoate.

The compositions are preferably substantially free of abrasives, as the compositions are typically not scrubbed onto teeth. When using abrasive toothpastes, people typically brush for less than 60 seconds, which is not enough time for the active ingredients to perform their intended activity. On the other hand, scrubbing teeth with an abrasive material for an extended period of time can be harmful in some cases. Therefore, in order to allow for extended application, the inventive compositions will preferably not include substantial quantities of an abrasive.

The compositions are preferably used with a dental tray that is thin-walled, flexible and lightweight. Such trays can be held by the dental composition in position adjacent to the person's tooth surfaces to be treated. The preferred dental tray should be adapted for maximum comfort and will exert little if any significant mechanical pressure onto the person's teeth or gums. Accordingly, when used with a tray, the dental whitening compositions will preferably be sufficiently sticky, viscous and resistant to dilution by saliva such that they can act as a glue and reliably adhere and retain the dental tray over the person's teeth for varying time durations. Nevertheless, although such dental trays are preferred, any conventional dental trays may also be utilized. In addition, the inventive dental compositions can be applied directly to a person's teeth without a tray. In such cases, higher concentrations of the dental agent(s) will preferably be used in order to speed up the desired action or results of the dental agent(s).

Any component other than the active dental agents, such as the potassium nitrate, bleaching agent, antimicrobial agent, and anticariogenic agent, shall comprise the "carrier". In the case where the dental composition is sticky and viscous, the carrier will include a sticky matrix material formed by combining a sufficient quantity of a tackifying agent, such as carboxypolymethylene, with a solvent, such as glycerin, polyethylene glycol, or water. Although the carrier is preferably formed by combining a tackifying agent and a solvent, the carrier may comprise a solvent without a tackifying agent in some embodiments Preferred compositions, as described hereinbelow, are relatively sticky and glue-like to enable a preferred dental tray to be held and retained against a person's teeth. Preferred carriers are preferably safe for oral use, do not readily dissolve in saliva, and do not react with the tooth opacifying agent.

In addition to carboxypolymethylene, examples of other suitable tackifying agents, or thickening agents that can assist other tackifying agents, include xanthan gum, talha gum, tragacanth gum, carboxymethylcellulose, locust bean gum, guar gum, Irish moss gum, ghatti gum, furcelleran gum, carrageenan gum, arabic gum, alginic acid gum, agar gum, aiginate gum, PEMULEN®, a proprietary compound of B.F, Goodrich, POLYOXN®, a mixture of polyethylene oxides having a molecular weight of 100,000–8,000,000 and available from Union Carbide, or any compositional or chemical equivalents of the foregoing. PEMULEN® is a propriety formula that includes a significant quantity of a polyacrylic copolymer that has a slightly hydrophobic end and a strongly hydrophilic end.

In addition to glycerin, many other polyols may serve as suitable solvents. The solvent may also be water alone or in combination with a polyol. Glycerin is a preferred solvent as it works well in forming a sticky gel with carboxypolymethylene. Glycerin also provides some flavor enhancement. A few possible substitutes for glycerin include propylene glycols, polypropylene glycol, polyethylene glycols, eryrthritol, sorbitol, mannitol, other polyols, and the like. In some embodiments polyols such as glycerin, polyethylene glycols, polypropylene glycol, propylene glycol, and sorbitol may also be used without a tackifying agent.

As indicated hereinabove, one currently preferred sticky matrix material includes a mixture of carboxypolymethylene together and other suitable admixtures. The term "carboxypolymethylcne" is used to denote a broad category of polymers, particularly copolymers of acrylic acid and polyallyl sucrose. Because carboxypolymethylene that has not been completely neutralized includes carboxylic acid groups or moieties, carboxypolymethylene can be classified as a weak acid. When dispersed in water, carboxypolymethylene can have a pH as low as about 2.5.

Because highly acidic compositions can etch teeth, it is generally preferable to adjust the pH of dental compositions that include carboxypolymethylene or other acids to make them less acidic. Accordingly, it is preferable to adjust the pH of compositions that include carboxypolymethylene to within a range from about 4 to about 9, more preferably to within a range from about 5 to about 7. Because it is contemplated that the carboxypolymethylene used in the matrix material and the compositions of the present invention will be mixed with a base to raise the pH of the resulting dental composition, the term "carboxypolymethylene" shall include carboxypolymethylene polymers within compositions at any pH.

The matrix material can include other optional components in addition to the carboxypolymethylene in order to provide bulk and also to yield a matrix material having the desired level of stickiness. One such admixture is glycerin, which is easily mixed with carboxypolymethylene. Another optional component is water, as set forth above. It is preferable to use a base in order to adjust the pH of the matrix material. Preferred bases can include inorganic bases such as sodium hydroxide or ammonium hydroxide. Alternatively, the base may include an organic base such as triethanolamine or other organic amines.

Since peroxides may cause irritation and also greater sensitivity in teeth for some people, the simultaneous inclusion of potassium nitrate can offset the potentially negative effects of the peroxide. Accordingly, potassium nitrate can simultaneously provide both opacification and desensitization. Other desensitizing agents can also be used to desensitize teeth, including citric acid, citric acid salts, strontium chloride, and the like. Since the present invention allows for prolonged contact via the use of an appropriate tray and/or a sticky composition, desensitizing agents in the composition are able to penetrate through the enamel.

In a preferred embodiment, the opacifying dental compositions within the scope of the present invention will be sufficiently sticky and (generally viscous such that positive pressure is needed to dispense them from the container; gravity is not sufficient. Unlike conventional low-viscosity compositions such as GLY-OXIDE (manufactured by Marion Laboratories) or PROXIGEL (manufactured by Reed and Carnick according to U.S. Pat. No. 3,657,413 to Rosenthal), prefelTed whitening compositions according to the present invention will be packaged within a syringe, squeezable tube, or other similar positive pressure dispensing device.

An improved dental tray that is thin-walled, flexible and lightweight for holding the dental composition adjacent to a person's teeth is preferably used in combination with sticky and viscous dental whitening compositions of the present invention. The general process for preparing such dental trays is as follows. First, an alginate impression which registers all teeth surfaces plus the gingival margin is made and a stone cast is made of the impression. Optional reservoirs can be prepared by building a layer of rigid material on the stone cast on specific teeth surfaces to be treated. A dental tray is then vacuum formed from the modified cast using a thin, flexible plastic sheet material. Once formed, the tray is preferably trimmed barely shy of the gingival margin on both the buccal and lingual surfaces of the person's teeth. The resulting tray provides a comfortable fit of the person's teeth with optional reservoirs or spaces located where the rigid material was placed on the stone cast. The trays can optionally overlap the gums if desired to provide contact between the dental compositions and a person's gums. The trays of the present invention have greatly increased comfort and exert little or no significant mechanical pressure on a person's teeth or gums. Instead, sticky dental compositions within the scope of the invention can act like a glue to hold the improved trays in place.

The amount of tooth whitening obtained through the use of the inventive compositions and methods is dependent primarily upon (1) the length of time each day the tray is worn; and (2) the number of days the tray is worn. The treatment schedule may be tailored to each person's lifestyle or response to the treatment and can be performed as often as a person desires to provide effective relief from excessively translucent teeth. It has been found that treatment during sleep is a good treatment period since there is less mouth activity which causes less whitening composition to be pumped from the tray.

Accordingly, an object of the present invention is to provide compositions and methods for treating excessively translucent teeth.

It is another object to provide compositions for treating excessively translucent teeth which can optionally include other dental agents, such as bleaching agents, antimicrobial agents or anticariogenic agents.

It is a further object to provide compositions for bleaching teach that include a desensitizing agent for offsetting the tendency of peroxide bleaching agents to make teeth more sensitive.

Finally, it is an object and feature of this invention to provide compositions for treating excessively translucent teeth that are sufficiently sticky and resistant to dilution by saliva such that they have the ability to adhere and retain a flexible, thin-walled dental tray against a person's teeth, wherein the dental tray does not exert significant mechanical pressures onto the person's teeth or gums.

These and other objects and features of the present invention will become more fully apparent from the description as follows, or may be learned by the practice of the invention.

BRIEF DESCRIPTION OF THE DRAWINGS

FIG. 1 is a perspective view of a stone cast of a patient's teeth with a coating being applied to selected teeth surfaces.

FIG. 2 is a perspective view of the stone cast of FIG. 1 with a dental tray formed from the cast and trimmed below the gingival margin.

FIG. 3 is a cross-sectional view taken along line 3—3 of FIG. 2.

FIG. 3A is an enlarged close-up view taken within the section line 3A—3A of FIG. 3.

DETAILED DESCRIPTION OF THE PREFERRED EMBODIMENTS

Figure 4:
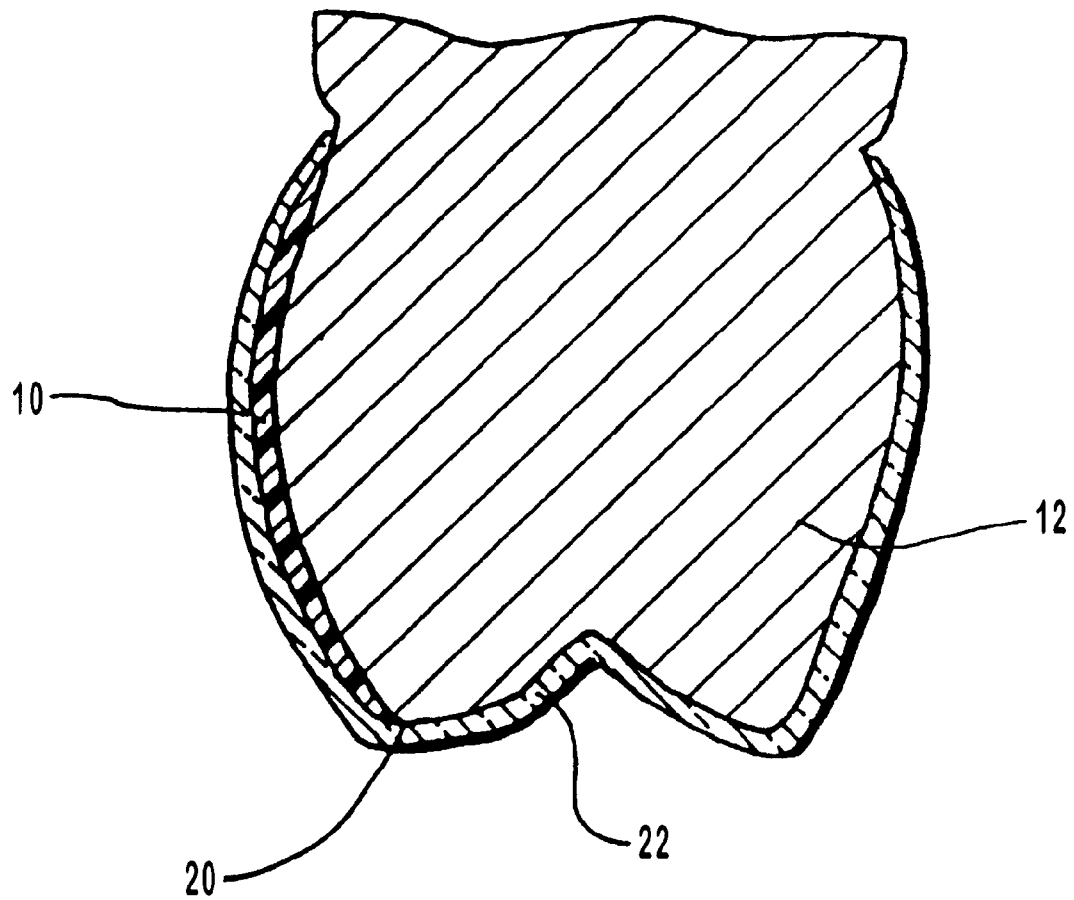
FIG. 4 is a cross-sectional view taken along line 4—4 of FIG. 2.

As summarized above, the present invention generally relates to dental whitening compositions and methods for treating excessively translucent teeth. At a minimum, the inventive compositions will include potassium nitrate, which can act as either an opacifying agent, a desensitizing agent, or both. The potassium nitrate is delivered to the teeth by means of a carrier, which includes any component other than the active dental agent(s). In some embodiments, the inventive compositions may include a bleaching agent, such as carbamide peroxide, hydrogen peroxide, and the like in order to further whiten a person's teeth. In such cases, the desensitizing properties of the potassium nitrate can assist in reducing sensitivity that may be caused in some people by the bleaching agent. The compositions may also include an anticariogenic agent or antimicrobial agent. The compositions are preferably abrasiveless as the compositions are not typically scrubbed onto a person's teeth for 60 seconds or less like typical toothpastes.

In a preferred embodiment, the dental whitening compositions will be used in conjunction with a thin, flexible, comfortable-fitting dental tray in order to hold the compositions against the person's teeth. Preferred dental trays will conform to the size and shape of a person's teeth and will exert little or no significant mechanical pressure onto the person's teeth and/or gums. This makes them more comfortable and pleasant to use compared to conventional dental trays. Nevertheless, the inventive tooth whitening compositions may certainly be used with conventional dental trays, or with no tray at all.

In the case where a thin, flexible dental tray is used, the potassium nitrate and optional dental agents will preferably be dispersed in a carrier containing a matrix material capable of exerting a glue-like action such that the whitening composition adheres and retains the tray to a person's teeth. The potassium nitrate may alternatively be placed directly onto the person's teeth without a tray, or by means of conventional dental trays that are held in place by mechanical fit.

The amount of potassium nitrate that is included within the whitening compositions of the present invention may vary depending on whether it is desired to desensitize, opacify or both. In general, it is possible to both desensitize and opacify at concentrations between about 0.1% to about 10% by weight of the dental composition. Nevertheless, concentrations up to 50% can be used in some cases in order maximize the speed and effects of the potassium nitrate, although good results are certainly possible at lower concentrations. Thus, the inventive compositions may preferably include potassium nitrate in a wide range from about 0.1% to about 50% by weight of the whitening composition, more preferably in a range from about 1% to about 25% by weight of the whitening composition, and most preferably in a range from about 3% to about 10% by weight of the whitening composition.

In addition to whitening teeth by increasing the opacity or decreasing the translucency of teeth, the potassium nitrate can act to decrease the sensitivity of teeth. The ability to decrease the sensitizing of teeth is particularly beneficial when the dental whitening composition also contains a bleaching agent such as carbamide peroxide, which has reportedly caused some people to experience increased sensitivity.

In a preferred embodiment, the carrier will include a tackifying agent and a solvent, which together yield a sticky matrix material, although a solvent may be used alone in some embodiments. The preferred matrix material will be sufficiently sticky to enable a preferred dental tray to be held and retained against a person's teeth. Various tackifying agents will be described hereinbelow.

Suitable sticky matrix materials are preferably safe for oral use and do not inactivate the potassium nitrate. They are preferably viscous and do not readily dissolve in saliva. One currently preferred tackifying agent used to form a sticky and viscous matrix material comprises carboxypolymethylene. Carboxypolymethylene can be used to form a glue-like dental whitening composition that itself can act as an adhesive in holding a comfortable, non-self-retaining dental tray against a person's teeth. The use of carboxypolymethylene eliminates the need to use dental trays that are self-retaining (i.e., typically trays that are rigid and which mechanically interlock over a person's teeth or gums and which are intended for use with less sticky compositions).

Carboxypolymethylene is a broad term that refers to vinyl polymers having active carboxyl groups. Suitable carboxypolymethylene compositions may be obtained from B.F. Goodrich Company under the tradename CARBOPOL®. Another tradename for carboxypolymethylene is CARBOMER®. In a commonly-sold form, carboxypolymethylene can have a pH as low as 2.5. As discussed below, the pH of compositions made with carboxypolymethylene can be raised to yield compositions that are less acidic.

The amount of carboxypolymethylene within the inventive dental whitening compositions can vary depending on the desired level of stickiness and also the identities and amounts of the other components within the dental composition. In general, the dental whitening compositions of the present invention will preferably include carboxypolymethylene in a concentration in a range from about 0.5% to about 25% by weight of the dental whitening composition, more preferably in a range from about 2% to about 12% and most preferably in a range from about 3% to about 10%. Where is it desired to increase the stickiness, viscosity and resistance to dilution to saliva, one may adjust the concentration of carboxypolymethylene to achieve a desired level of any or all of these properties. Increased stickiness assists in retaining the preferred dental trays against a person's teeth. Alternatively, compositions can be made less adhesive and tacky if desired, particularly is applied directly without a dental tray.

It should be understood, however, that the actual amount of carboxypolymethylene is not critical for obtaining a sticky, viscous dental composition. For example, the sticky matrix material may include other tackifying components that in combination with, or in lieu of some or all of, the carboxypolymethylcne will yield a dental whitening composition having the desired level of stickiness needed to hold a preferred, comfortable-fitting dental tray in place over a person's teeth. Other synthetic polymers and/or natural gums, proteins, or other gel-forming admixtures can be used so long as they yield a sticky dental whitening composition.

One currently preferred carboxypolymethylene resin is known by the tradename CARBOPOL 934P. CARBOPOL 934P is a high purity pharmaceutical grade of CARBOPOL 934, having an approximate molecular weight of about 3,000,000. In addition to thickening and suspending, CARBOPOL 934P has been used in dry tablets to impart sustained release properties Extensive toxicity studies have been conducted on CARBOPOL, 934P, and a master file has been established with the Food and Drug Administration. It is listed as CARBOMER 934P in the National Formulary. A more recently preferred carboxypolymethylene is CARBOPOL 974P NF, which has more recently surpassed CARBOPOL 934P as the carboxypolymethylene of choice. Although CARBOPOL 974P NF is similar or identical in molecular weight compared to CARBOPOL 934P, it is purified in a way that makes it more pharmaceutically acceptable material.

It is believed that other carboxypolymethylene resins, such as CARBOPOL 940, may be substituted for CARBOPOL 934P or CARBOPOL 974P NF. CARBOPOL 934P and CARBOPOL 974P NF are currently preferred because they are obtainable in a pharmaceutical grade.

In order to obtain good dispersion of the carboxypolymethylene resin within the dental whitening composition, it is recommended that the carboxypolymethylene be mixed with a suitable solvent before attempting to add other components that arc less compatible with carboxypolymethylene, such as water. Examples of suitable solvents for use with carboxypolymethylene include glycerin, other polyhydric alcohols, polyalkylene glycols and other polyols, and the like. Glycerin appears to enable larger quantities of carboxypolymethylene to be dispersed in water. It is preferable that the concentration of glycerin, polyol, or like substance utilized as a solvent in the dental whitening compositions be added in a range from about 15% to about 85% by weight of the dental whitening compositions, more preferably in a range from about 25% to about 75% by weight and most preferably in a range from about 30% to about 65% by weight.

Glycerin, other polyols, and the like are inexpensive solvents that work well in forming a sticky gel with carboxypolymethylene. The glycerin also provides some flavor enhancement such that a bland, sweet flavor is perceived. A few possible substitutes for glycerin include propylene glycols, polypropylene glycol, polyethylene glycols, other polyols. sorbitol, mannitol, eryrtliritol, other polyhydric alcohols, stearyl alcohol and other alcohols, and the like. Ethylene glycol would also work but is disfavored since it is toxic. In addition to acting as a solvent for the tackifying and thickening agents, hydrophilic solvents such as glycerin, polyethylene glycols, polypropylene glycol, propylene glycol, and sorbitol may also be used as a suitable carrier without a tackifyin, agent.

Water may also be included as a solvent within the compositions of the present invention, although more carboxypolymethylene must generally be added as water is added to maintain the same level of stickiness. The amount of water included within the dental whitening compositions of the present invention is preferably in a range from about 0% to about 50% by weight of the dental whitening composition, more preferably in a range from about 1% to about 45% by weight and most preferably in a range from about 2% to about 40% by weight. It will be appreciated that the total quantity of water in the dental whitening composition may come from different sources. For instance, some constituents such as dental agents and bases discussed below may come as aqueous solutions.

Because carboxypolymethylene is a polycarboxylic acid, it tends to lower the pH of the resulting dental whitening compositions significantly, down to a pH of about 2.5 in some cases. It appears, based upon clinical and in vitro testing, that dental whitening compositions with a pH below about 5 are able to etch enamel. To avoid etching enamel, it is preferable to add a neutralizing agent, or more specifically, a base in order to raise the pH of the inventive dental whitening compositions to within a pH range of about 4 to about 9. When such a composition is used having a pH at the lower or upper extremes of such a range the exposure period is preferably relatively brief. Accordingly, the pH is preferably adjusted to within a range from about 5 to about 8 and most preferably from about 6 to about 7. Inorganic and organic bases may be used, with the use of concentrated aqueous sodium hydroxide (50% NaOH in water) being one currently preferred embodiment. In addition to sodium hydroxides other inorganic bases may be used such as potassium hydroxide and ammonium hydroxide. Examples of suitable organic bases include alkyl amines such as triethanolamine, di-isopropanol amine and other similar amines. The amount of neutralizing agent or base to be included will generally depend on the desired pH and the amount of carboxypolymethylene in the dental whitening composition. Accordingly, neutralizing agents or bases are preferably included in a range from about 1% to about 12% by weight of the dental whitening composition, more preferably in a range from about 2% to about 8% by weight and most preferably in a range from about 3% to about 7% by weight.

The term "carboxypolymethylene" shall be understood to include carboxypoly-methylene resins regardless of the pH of the overall dental composition. In other words, the term "carboxypolymethylene" broadly includes resins that have been mixed with a base to raise the pH of the compositions. Moreover, he term "carboxypolymethylene" shall broadly include carboxypolymethylene resins that have reacted with, formed complexes with, or otherwise been altered in any way by other components within the dental whitening compositions of the present invention so long as the carboxypolymethylene is able to impart the desired level of stickiness and viscosity to the final dental whitening composition in combination with the other components within the dental whitening composition.

In addition to carboxypolymethylene, examples of other suitable tackifying and thickening agents include gums such as xanthan gum, talha gum, tragacanth gum, locust bean gum, guar gum, Irish moss gum, ghatti gum, furcelleran gum, carrageenan gum, arabic gum, alginic acid gum, agar gum, alginate gum. Another suitable tackifying agent is sold as PEMULEN®, a proprietary compound from B.F. Goodrich, or a compositional or chemical equivalent thereof. PEMULEN® includes a significant quantity of a polyacrylic copolymer that has a slightly hydrophobic end and a strongly hydrophilic end. Additional examples of suitable tackifying agents include polyethylene oxides such as POLYOX® sold by Union Carbide. These tackifying agents may be present in the same ranges as discussed above in relation to carboxypolymethylene.

It is also preferable to utilize a bleaching agent to enable the whitening composition to simultaneously bleach and opacify the teeth. Examples of suitable bleaching agents include hydrogen peroxide, carbamide peroxide, benzoyl peroxide, glyceryl peroxide and sodium perborate. A significant advantage of using potassium nitrate as an opacifying agent in combination with a bleaching agent in a tooth whitening composition is that the potassium nitrate simultaneously decreases the sensitivity of the teeth that may result from the use of the bleaching agent. The bleaching agents are preferably included in a range from about 0.5% to about 50% by weight of the dental whitening composition, more preferably in a range from about 1% to about 30% by weight and most preferably in a range from about 3% to about 20% by weight.

In order to preserve the stability of the dental whitening compositions, particularly when bleaching agents are included, it is often preferable to include an ion scavenger such as EDTA and salts of EDTA such as edetate disodium, oxine EDTA, calcium disodium EDTA, and others. Additionally, ion scavengers such as citric acid, succinic acid, adipic acid, nitrates and phosphates of tin and any other commonly-used chelating agents may be used. Ion scavengers are preferably included in an amount in a range from about 0% to about 1% by weight of the dental whitening composition, more preferably in a range from about 0.03% to about 0.5% by weight and most preferably in a range from about 0.05% to about 0.2% by weight.

It may also be preferable to include other active dental agents to provide other types of dental and/or gum treatment. For example, in conjunction with dental desensitization and/or opacification, it may be desired to provide an anti-cariogenic treatment. Preferred anticariogenic and antidemineralizing agents include fluoride salts, more particularly sodium monofluorophosphate, sodium fluoride, and stannous fluoride. Depending on the level of fluoride treatment desired, and depending on whether or not a composition is "over-the-counter" or "by prescription", the fluoride will be included in a range from about 0% to about 1% by weight of the dental whitening composition, more preferably in a range from about 0.1% to about 0.5% by weight.

Antimicrobial agents, e.g., for fighting gum disease, may be included in conjunction with the potassium nitrate or other opacifying agent. Examples of useful antimicrobial agents include chlorohexidine, tetracycline, cetyl pyridinium chloride, benzalkonium chloride, cetyl pyridinium bromide, methyl benzoate, and propyl benzoate. The antimicrobial agents are preferably included in an amount in a range from about 0% to about 15% with the dental whitening composition, more preferably in a range from about 1% to about 5% by weight.

As indicated hereinabove, the dental whitening compositions of the present invention preferably do not include an abrasive. Abrasives only externally treat a tooth; however, it is believed that opacification of a tooth is achieved by the action of the potassium nitrate internally within a tooth. Not only are abrasives unnecessary but inclusion of abrasives in the composition may be undesirable in preferred embodiments where it is desired for the whitening composition to remain on the teeth for an extended period of time (i.e., greater than about 3 minutes). It is common experience that toothpastes become quickly diluted by saliva and will not persist in a paste-like form for more than a short period of time (i.e., for more than about a minute).

Other suitable tooth desensitizing agents that may be used in addition to potassium nitrate according to the present invention include citric acid, citric acid salts, strontium chloride, and the like, as well as other desensitizing agents known in the art. The amount of desensitizing agent included within the dental whitening compositions of the present invention may vary according to the concentration of the potassium nitrates, the desired strength and intended treatment times. Accordingly, if included at all, the other desensitizing agents will preferably be included in an amount in a range from about 0.1% to about 10% by weight of the dental desensitizing composition, more preferably in a range from about 1 to about 7% by weight.

One currently preferred method of dispensing sticky and viscous dental whitening compositions within the scope of the present invention is by means of a syringe. Squeezable tubes and other similar dispensing devices may also be used to dispense the compositions. Upon dispensing, the dental whitening compositions are sufficiently viscous that they do not easily settle or spread once dispensed, but will generally remain as a single extruded strand or bead of dental whitening composition. Nevertheless, bottles, tubes or other dispensing means known in the art may be used, particularly where the whitening composition has lower viscosity, low stickiness, and does not include a thickening agent.

It is currently preferred to provide a unit dose of the dental whitening compositions in a syringe or similar dispensing device. In this way, the person can load the precise amount of dental whitening composition onto the dental tray for each treatment period. By using such dispensing devices, the dentist is also able to monitor how many doses the person has received and used.

Although not required, sticky and viscous dental whitening compositions of the present invention are preferably used to treat a person's teeth in conjunction with dental trays that exert little or no significant mechanical pressure onto a person's teeth and gums. The result is a more comfortable and pleasant feeling dental tray, unlike prior art dental trays which are generally rigid and/or thick-walled such that they exert sufficient mechanical pressures onto the teeth and/or gums to be "self-retaining". In some embodiments, however, the whitening compositions can be applied directly to the person's teeth without a dental tray, or a less viscous and sticky whitening composition according to the invention may be used in conjunction with self-retaining trays known in the art.

In the general process for preparing preferred dental trays according to the present invention, an alginate impression is made which registers all teeth surfaces plus the gingival margin. Thereafter, a stone cast is made of the impression. Excess stone can be trimmed away for easy manipulation and forming the dental tray.

Reference is now made to FIGS. 1–4. In a preferred method for forming a dental tray, one or more reservoirs can be formed in the resultant dental tray by applying a thin coating 10 of a rigid material to the stone cast 12 corresponding to teeth where it is desired to provide more of the dental whitening composition. As depicted in FIG. 1, the coating 10 may be applied using a brush tipped applicator 14. The coating may also be light curable for convenience. In those instances where the dental tray is to be trimmed below the gingival margin, the coating material will preferably be applied in a manner that is kept at a distance greater than about 1 mm from the gingival line 16, more preferably in a range from about 1.25 to about 1.5 mm from the gingival line 16.

The finished coating will have a thickness corresponding to the desired reservoir depth, which will commonly be about 0.5 mm. It is generally preferred that the rigid coating material not be applied over the stone cast corresponding to the incisal edges 18 and occlusal edges 20 of the person's teeth. This because it is preferable for the incisal edges and occlusal edges of the person's actual teeth to contact the finished tray in order to prevent or reduce vertical movement of the tray during use, which movement could act as a pump that could express the dental whitening composition from the tray and result in the intake of saliva within the dental tray.

A dental tray 22 is then vacuum formed from the stone cast using conventional techniques. The dental tray 22 is preferably constructed of a soft transparent vinyl material preferably having a preformed thickness in a range from about 0.2 mm to about 1.5 mm, more preferably in a range from about 0.25 mm to about 1 mm. Soft materials yield dental trays that are more comfortable for the patient to wear. It will be appreciated that the final tray thickness may vary depending on the technique used to prepare the tray, as well as the size and shape of the personas teeth. Patients suspected of being breuxers or hard biters may require either a thicker or a harder material. Of course, patients should be counselled not to eat with trays in place or to bite firmly into them.

Once formed, the dental tray 22 is preferably trimmed barely shy of the gingival margin 16 of the person's teeth on both the buccal and lingual surfaces for maximum comfort. Enough tray material should be left to assure that the teeth will be covered to within about ¼ mm to about ⅓ mm of the gingival border upon finishing and beveling of the tray periphery. It is also generally preferred to scallop up and around the interdental papilla so that the finished tray does not cover them. The tray edges are preferably smoothed so that the lip and tongue will not feel an edge prominence. Slight adjustments to the tray may be made by carefully heating and stretching the tray material.

Figure 5:
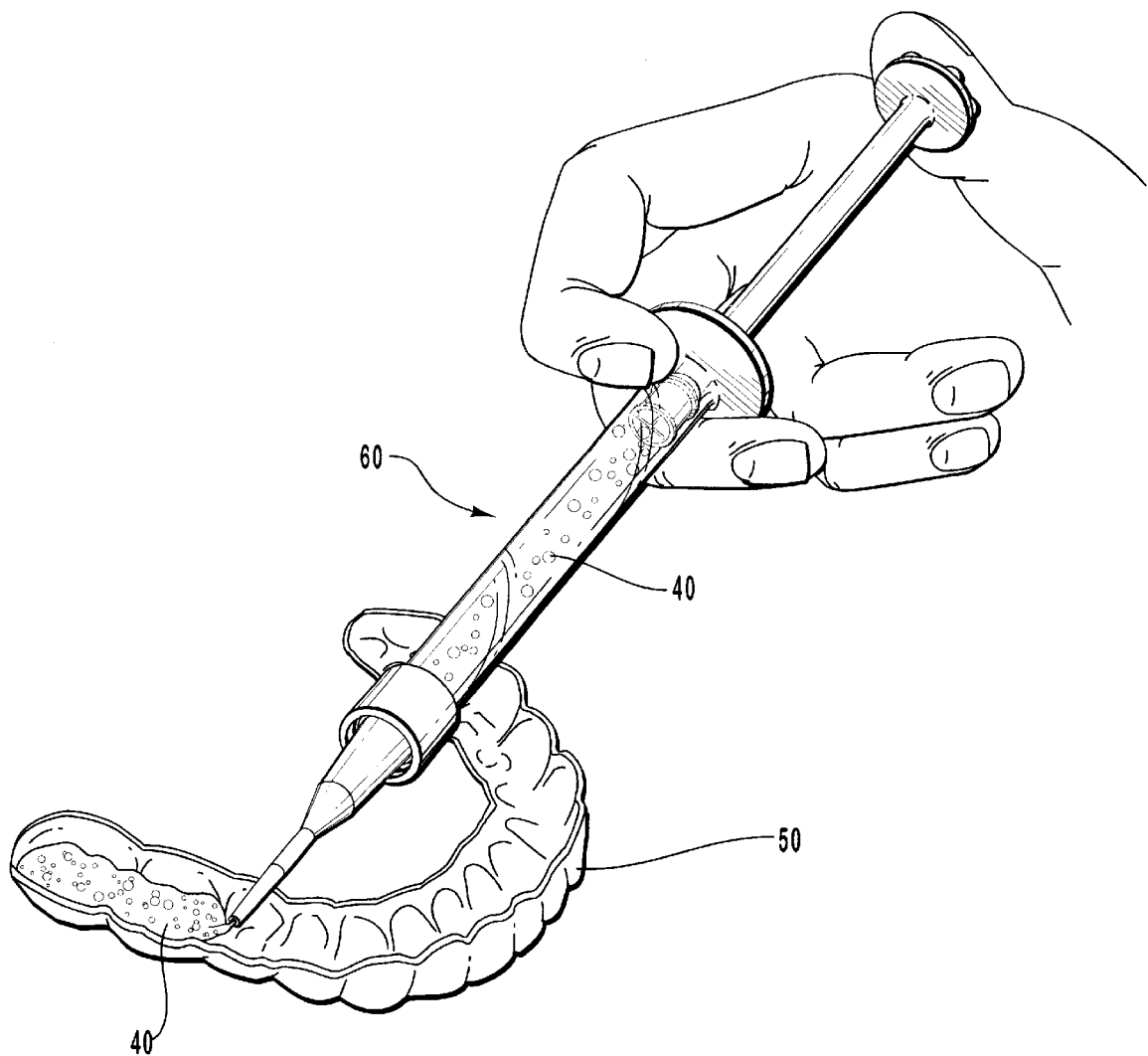
FIG. 5 is a perspective view of the opacifying composition being delivered from a syringe into a thin-walled, flexible dental tray.
Figure 6:
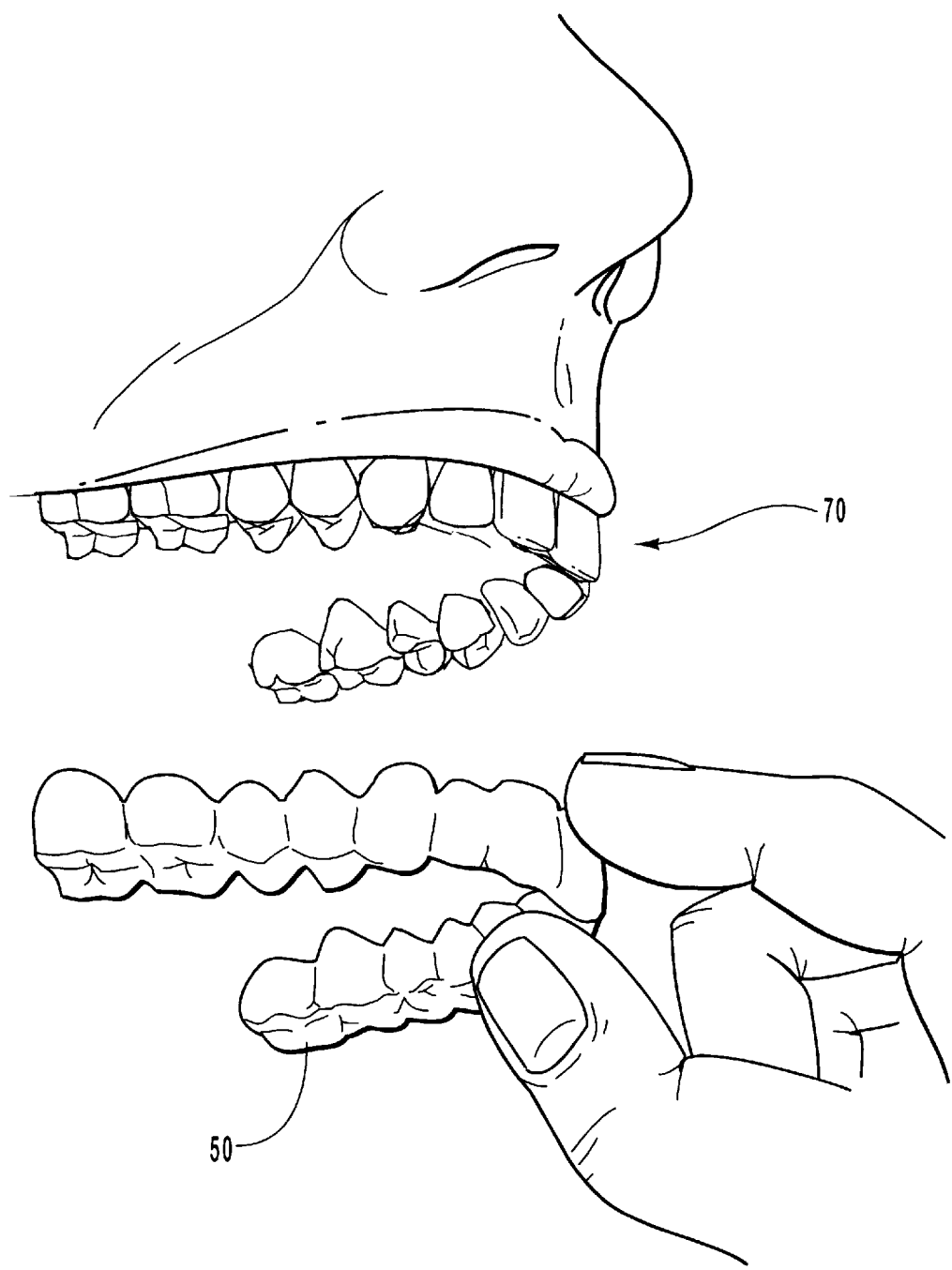
FIG. 6 is a perspective view of a thin-walled, flexible dental tray filled with the opacifying composition just before being positioned on a patient's upper arch.
Figure 7:
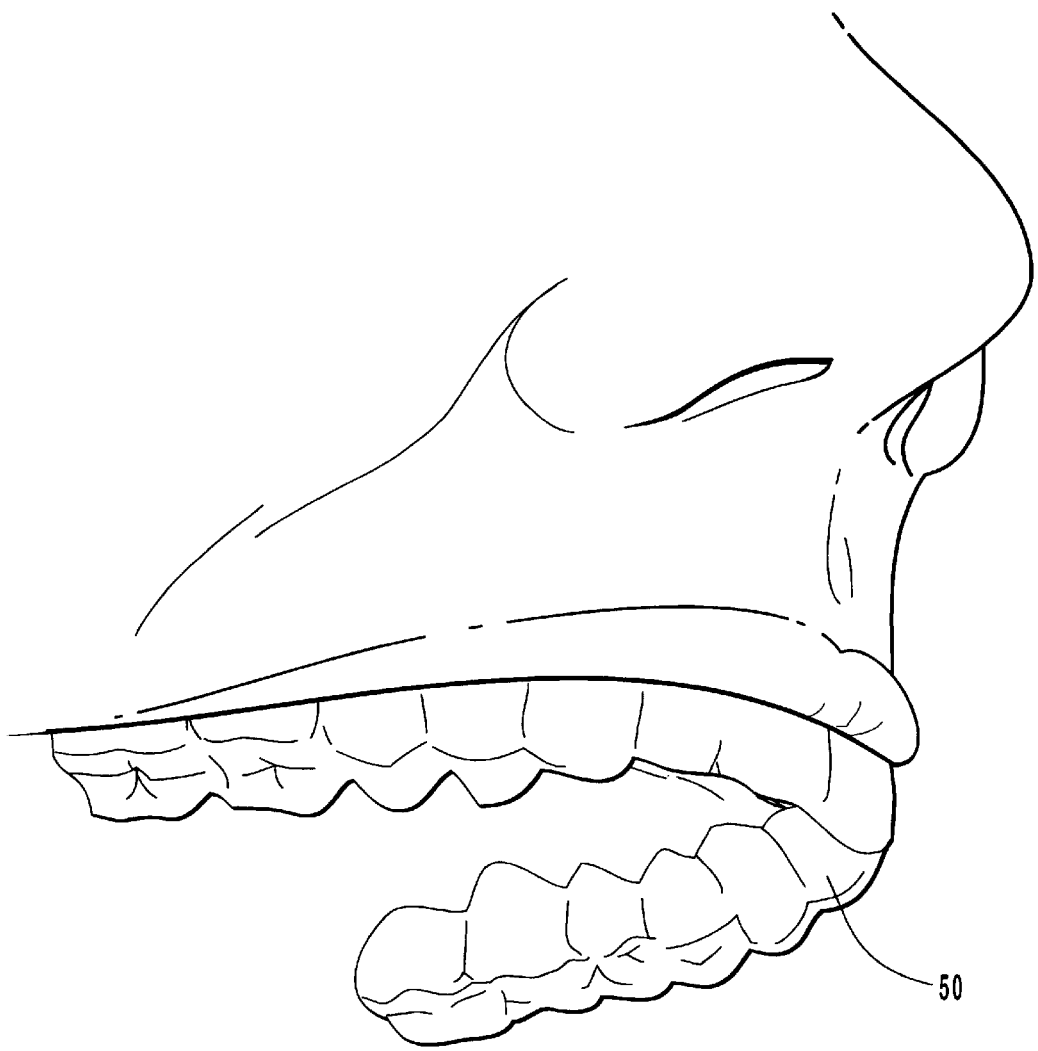
FIG. 7 is a perspective view of a thin-walled, flexible dental tray filled with the opacifying composition positioned on a patient's upper arch.

Reference is now made to FIGS. 5–7. FIG. 5 depicts the dental whitening composition 40 being deposited into a dental tray 50 from a syringe 60. FIG. 6 depicts dental tray 50 being inserted onto an arch 70 in a patient's mouth. FIG. 7 depicts dental tray 50 in position on the teeth of arch 70. The dental composition may be deposited throughout the dental tray to contact the entire arch or may be deposited within a portion of the tray to only contact a portion of the arch. Additionally, the dental tray may be configured to only contact a portion of an arch or only a single tooth. While depositing the dental whitening composition into dental tray 50 as shown in FIG. 5 is the preferred method, the dental whitening composition may also alternatively be deposited directly onto the teeth and then tray 50 may be positioned on the teeth of arch 70.

From practice, it has been found that patients may experience less tooth discomfort from tray pressures when using a tray with reservoirs built into the tray as described above. It is currently believed this is due to the fact that the teeth are not held as firmly by the tray, so "orthodontic" pressures experienced by teeth from tray discrepancies are minimized. The use of thin, soft tray materials minimize mechanical forces applied to teeth or gums compared to the harder or thicker plastics known in the art. Reservoirs, of course, can provide more of the dental whitening composition against the person's teeth and can also assist in seating the dental tray over the person's teeth.

Although the aforementioned thin, flexible dental trays are preferred when treating a person's teeth, it may be preferable in some cases to allow the dental tray to overlap the person's gums in the case where dental agents are included to fight gum diseases. Of course to the extent that the dental whitening compositions do not irritate the gums, the dental trays can always be constructed to overlap the gums.

Nevertheless, it has been found that where it is desired to treat a person's teeth rather than the gums, it is generally more comfortable for the patient if the dental tray has been trimmed to or below the gingival margin. Even in those cases where the dental trays will overlap the person's gums, the dental trays of the present invention preferably will not exert significant mechanical pressure onto the person's gums.

Because the preferred dental trays described herein can be made to exert little or no mechanical pressure onto a person's teeth and gums, it will be important in such cases for the inventive dental whitening compositions to be able to act like a glue to reliably adhere and retain the dental tray over a person's teeth for the desired length of treatment. Accordingly, the dental whitening compositions will preferably have a stickiness such that they can reliably adhere and retain a dental tray over a person's teeth for at least about one hour without significant mechanical pressure from the dental tray, more preferably for at least about two hours, and most preferably for at least about four hours. Nevertheless, while the foregoing time durations are given in order to provide an accurate measurement of the stickiness of the dental whitening compositions of the present invention, they should not be taken to be a limitation as to the actual length of time that the patient may wish to use the inventive dental whitening compositions. While a given dental whitening composition may be able to retain the dental tray against a person's teeth for, e.g., 10 hours or more, that composition could certainly be used within the scope of the present invention for any desired time period, such as for 15 minutes, one hour, or any desired time duration.

The dental whitening compositions of the present invention may be used at any time and for any duration by a person that desires to make his or her teeth less translucent and more white. Although the dental whitening compositions of the present invention facilitate the use of flexible, thin-walled dental trays that are more comfortable to use compared to prior dental trays, the insertion of any dental tray within a person's mouth will cause some alteration of behavior and diminution of the freedom to use one's mouth. Therefore, in order to maximize treatment time and reduce the inconvenience of having a dental tray lodged within a person's mouth, it is recommended to use the dental trays at night during a personas sleep.

Although long exposure times may be desired in some cases, it has been found that optimal results may be achieved from cyclic exposure periods involving repeated exposures over several days. For example, the treatment regime may alternatively entail exposure for a period of time such as an hour without further exposure until the subsequent day. For day use, it is recommended that the whitening compositions be applied for about 1 to 3 hours. The length of the treatment period during night use may vary with the sleep pattern of the particular person and may accordingly be between about 5 to 9 hours.

Although it is recommended that the dental whitening compositions of the present invention may be applied and allowed to contact teeth for several hours, much shorter periods of time, even as brief as 3 minutes, result in some degree of opacification. Obviously when a patient's teeth are exposed to the whitening compositions for only brief periods such as about 5 to 15 minutes, the rate of opacification will usually be much slower than when the exposure time is an hour or several hours.

The use of dental trays is preferred as extended contact between the composition and the teeth is enabled through the support and protection of the tray. Elowever, other methods of contacting teeth with the inventive dental whitening composition are also within the scope of the invention in addition to the use of the dental whitening composition with a dental tray. For example the dental whitening composition can be merely deposited onto a tooth or several teeth during one or more dental office visits. In such an application, the dental whitening composition is sufficiently sticky and viscous to stay in contact with the tooth or teeth to be whitened for a period of time of at least about three minutes without significant agitation of the composition against the tooth or teeth.

The dental whitening composition may be used with rubber dams and resin barriers, particularly when the composition includes bleaching agents. More particularly, the dental whitening composition may be used in combination with rubber dams and resin barriers when the method involves high concentrations of bleaching agents or rapid whitening which involves directing heat or light to the bleaching composition. Examples of such rubber dams and resin barriers are disclosed in U.S. patent application Ser. No. 08/802,674, entitled "Polymerizable Isolation Barriers and Methods for Forming and Using such Barriers" and filed on Feb. 19. 1997, which is hereby incorporated by reference. The preferred resin barrier is sold by Ultradent Products, Inc. under the mark OPALDAM™. The preferred rubber dam is sold under the mark DERMADAM™ and is preferably used in conjunction with caulking and putty materials sold under the mark ORASEAL®, all of which arc available from Ultradent Products, Inc.

In order to more clearly illustrate the parameters of the inventive dental whitening compositions within the scope of the present invention, the following examples are presented. The following examples are intended to be exemplary and should not be viewed as limiting to the scope of the invention.

EXAMPLE 1

A whitening composition within the scope of the present invention was prepared by combining the following ingredients in the following proportions, measured as percentage by weight of the whitening composition:

| | |
|---|---|
| CARBOPOL 974P NF | 6.8% |
| Glycerin | 48.45% |
| Polyethylene glycol 300 | 5.5% |
| Water | 20.0% |
| Sodium hydroxide (50%) | 5.4% |
| $KNO_3$ | 3.0% |
| Carbamide peroxide | 10.5% |
| Disodium EDTA | 0.1% |
| NaF | 0.25% |

The CARBOPOL 974P NF was obtained from B.F. Goodrich Company in Cleveland, Oh. The CARBOPOL 974P NF was first combined with the glycerin and polyethylene glycol 300 then mixed with the water. Mixing glycerin and polyethylene glycol 300 within the CARBOPOL, 974P NF enabled it to be more easily mixed with the water. The $KNO_3$, carbamide peroxide and disodium EDTA were added to the mixture. after which the sodium hydroxide was blended into the homogeneous composition in order to raise the pH to an acceptable level. The sodium fluoride was then added. The resulting dental whitening composition had opacifying, bleaching, desensitizing and anticariogenic properties, and was sufficiently sticky that it could reliably hold and maintain a dental tray against a person's teeth without significant mechanical pressure being exerted by the tray onto a person's teeth and gums.

EXAMPLE 2

A sticky opacifying dental whitening composition within the scope of the present invention was made according to the procedure of Example 1, except that more $KNO_3$ was included and slightly less glycerin was added such that the remaining components were combined in the following amounts as a percentage by weight of the composition:

| | |
|---|---|
| CARBOPOL 974P NF | 6.8% |
| Glycerin | 46.45% |
| Polyethylene glycol 300 | 5.5% |
| Water | 20.0% |
| Sodium hydroxide (50%) | 5.4% |
| KNO$_3$ | 5.0% |
| Carbamide peroxide | 10.5% |
| Disodium EDTA | 0.1% |
| NaF | 0.25% |

The foregoing procedure resulted in a dental whitening composition. The resulting dental whitening composition had more opacifying and desensitizing capability than the composition of Example 1. The composition was sufficiently sticky that it could reliably hold and maintain a dental tray against a person's teeth without significant mechanical pressure on the patient's teeth and gums as in Example 1.

EXAMPLE 3

A dental whitening composition within the scope of the present invention is made according to the procedure of Example 1, except that the ingredients are combined in the following, concentrations by weight percent:

| | |
|---|---|
| CARBOPOL 974P NF | 6.8% |
| Glycerin | 40.55% |
| Polyethylene glycol 300 | 5.5% |
| Water | 21.0% |
| Sodium hydroxide (50%) | 5.4% |
| KNO$_3$ | 5.0% |
| Carbamide peroxide | 15.5% |
| Disodium EDTA | 0.1% |
| NaF | 0.15% |

The foregoing procedure results in a sticky dental whitening composition having more opacifying, desensitizing and bleaching capability than the composition of Example 1, but with slightly less anticariogenic capability.

EXAMPLE 4

A dental whitening composition within the scope of the present invention is made according to the procedure of Example 1, except that the glycerin is replaced by propylene glycol. The ingredients are combined in the following concentrations by weight percent:

| | |
|---|---|
| CARBOPOL 974P NF | 6.8% |
| Propylene Glycol | 48.45% |
| Polyethylene glycol 300 | 5.5% |
| Water | 20.0% |
| Sodium hydroxide (50%) | 5.4% |
| KNO$_3$ | 3.0% |
| Carbamide peroxide | 10.5% |
| Disodium EDTA | 0.1% |
| NaF | 0.25% |

The foregoing procedure results in a sticky dental whitening composition capable of holding and maintaining a dental tray against a person's teeth in essentially the same manner as in Example 1. The opacifying, desensitizing, bleaching and anticariogenic capabilities are similar to those using the composition of Example 1.

EXAMPLE 5

A dental whitening composition within the scope of the present invention is made according to the procedure of Example 1, except that the ingredients are combined in the following concentration by weight percent:

| | |
|---|---|
| CARBOPOL 974P NF | 6.8% |
| Glycerin | 68.85% |
| Sodium hydroxide (50%) | 5.4% |
| KNO$_3$ | 8.0% |
| Carbamide peroxide | 10.5% |
| Disodium EDTA | 0.2% |
| NaF | 0.25% |

The foregoing procedure results in a sticky dental whitening composition capable of holding and maintaining a dental tray against a person's teeth in essentially the same manner as in Example 1. The composition has a higher level of opacifying activity and desensitizing capability compared to the compositions of Examples 1–4.

EXAMPLE 6

A dental whitening composition within the scope of the present invention is made according to the procedure of Example 1, except that the ingredients are combined in the following concentrations by weight percent:

| | |
|---|---|
| Polyethylene glycol 300 | 5.5% |
| Propylene Glycol | 45.2% |
| Water | 30.0% |
| PEMULEN ® TR-1 NF | 6.8% |
| Sodium hydroxide (50%) | 5.4% |
| KNO$_3$ | 3.0% |
| Hydrogen peroxide (30%) | 4.0% |
| Citric acid | 0.1% |

The foregoing procedure results in a sticky dental whitening composition having a lower viscosity compared with the composition in Example 1. The composition has a similar level of opacifying capability and slightly more effective bleaching capability than the composition of Example 1.

EXAMPLE 7

A dental whitening composition within the scope of the present invention is made according to the procedure of Example 1, except that the ingredients are combined in the following concentrations by weight percent:

| | |
|---|---|
| CARBOPOL 974P NF | 6.8% |
| Glycerin | 57.35% |
| Polyethylene glycol 300 | 5.5% |
| Propylene glycol | 20% |
| Triethanolamine | 8.0% |
| KNO$_3$ | 1.0% |
| Sodium perborate | 21.0% |
| Disodium EDTA | 0.1% |
| Sodium monofluorophosphate | 0.25% |

The foregoing procedure results in a sticky dental whitening composition having opacifying capability and desensitizing capability in a basic environment.

EXAMPLE 8

A dental whitening composition within the scope of the present invention is made according to the procedure of Example 1, except that the ingredients are combined in the following concentrations by weight percent:

| | | |
|---|---|---|
| CARBOPOL 974P NF | 6.8% | |
| Glycerin | 59.2% | |
| Polyethylene glycol 300 | 5.5% | |
| Water | 20.0% | |
| Sodium hydroxide (50%) | 5.4% | |
| $KNO_3$ | 3.0% | |
| Disodium EDTA | 0.1% | |

The foregoing procedure results in a sticky dental whitening composition capable of holding and maintaining a dental tray against a person's teeth in essentially the same manner as in Example 1. The composition has desensitizing and opacifying capabilities which are similar to those of the composition of Example 1.

EXAMPLE 9

A dental whitening composition within the scope of the present invention is made saccording to the procedure of Example 1, except that the ingredients are combined in the following concentrations by weight percent:

| | | |
|---|---|---|
| Glycerin | 50.8% | |
| Distilled Water | 30% | |
| Xanthan gum | 1.0% | |
| $KNO_3$ | 3.0% | |
| Carbamide peroxide | 15.0% | |
| Disodium EDTA | 0.2% | |

The foregoing procedure results in a dental whitening composition having similar opacifying and desensitizing capabilities compared to the composition of Example 1. The composition is less sticky than the composition of Example 1 and has greater bleaching capability.

EXAMPLE 10

A dental whitening composition within the scope of the present invention is made according to the procedure of Example 1, except that the ingredients are combined in the following concentrations by weight percent:

| | | |
|---|---|---|
| Glycerin | 87.0% | |
| $KNO_3$ | 3.0% | |
| Carbamide peroxide | 15.0% | |

The foregoing procedure results in a dental whitening composition having similar opacifying and desensitizing capabilities compared to the composition of Example 1. However, the composition is less sticky than the composition of Example 1 and has greater bleaching capability.

EXAMPLE 11

A dental whitening composition within the scope of the present invention is made according to the procedure of Example 1, except that the ingredients are combined in the following concentrations by weight percent:

| | | |
|---|---|---|
| Glycerin | 97.0% | |
| $KNO_3$ | 3.0% | |

The foregoing procedure results in a dental whitening composition having similar opacifying and desensitizing capabilities compared to the composition of Example 1. The composition has a lower viscosity and is less sticky than the composition of Example 1.

EXAMPLE 12

A dental whitening composition within the scope of the present invention is made according to the procedure of Example 1, except that the ingredients are combined in the following concentrations by weight percent:

| | | |
|---|---|---|
| Propylene glycol | 40.0% | |
| Polyethylene glycol 8000 | 5.0% | |
| Polyethylene glycol 600 | 27.0% | |
| Water | 7% | |
| $KNO_3$ | 6.0% | |
| hydrogen peroxide (30%) | 15.0% | |

The foregoing procedure results in a dental whitening composition that is less sticky and has a lower viscosity than the composition of Example 1. The composition is able to impart a higher degree of opacification, desensitization, and bleaching compared to the composition of Example 1.

EXAMPLE 13

A dental whitening composition within the scope of the present invention is made according to the procedure of Example 1, except that the ingredients are combined in the following concentrations by weight percent:

| | | |
|---|---|---|
| Glycerin | 30.0% | |
| Propylene glycol 300 | 30.0% | |
| $KNO_3$ | 5.0% | |
| Sodium perborate | 35.0% | |

The foregoing procedure results in a dental whitening composition that is less sticky and has a lower viscosity than the composition of Example 1. The composition is able to impart a higher degree of opacification, desensitization, and bleaching compared to the composition of Example 1.

EXAMPLE 14

A dental whitening composition within the scope of the present invention is made according to the procedure of Example 1, except that the ingredients are combined in the following concentrations by weight percent:

| | | |
|---|---|---|
| Propylene glycol | 47.5% | |
| Polyethylene glycol 300 | 30.0% | |
| $KNO_3$ | 2.5% | |
| Carbamide peroxide | 20.0% | |

The foregoing procedure results in a dental whitening composition that is less sticky and has a lower viscosity than the composition of Example 1. The composition has about the same opacifying and desensitizing capability but greater bleaching capability compared to the composition of Example 1.

EXAMPLE 15

To any of the foregoing dental whitening compositions is added one or more of the following antimicrobial agents for treatment of a patient's gums: chlorohexidine, tetracycline, cetyl pyridinium chloride, benzalkonium chloride, cetyl pyridinium bromide. methyl benzoate, and propyl benzoate. These compositions are preferably used in conjunction with a thin walled, flexible dental tray that overlaps the person's gums in order for the dental whitening compositions to contact the gums being treated.

EXAMPLE 16

To any of the foregoing dental whitening compositions which include a bleaching agent and do not include a bleaching agent stabilizer, one of the following chelating agents may be added: EDTA, monosodium EDTA, citric acid, succinic acid, and adipic acid.

From the foregoing, it will be appreciated that the present invention provides compositions and methods for treating excessively translucent teeth to opacify and thereby whiten the teeth.

The present invention also provides dental whitening compositions for treating excessively translucent teeth which optionally include other dental agents for treating teeth and/or gums, such as bleaching, antimicrobial or anticariogenic agents.

The present invention also provides dental whitening compositions for bleaching teeth while relieving excessive sensitivity of a person's teeth.

Finally. the present invention provides compositions for treating excessively translucent teeth that can be sufficiently sticky and resistant to dilution by saliva such that they have the ability to adhere and retain a flexible, thin-walled dental tray against a person's teeth, wherein the dental tray does not exert significant mechanical pressures onto the person's teeth or gums.

The present invention may be embodied in other specific forms without departing from its spirit or essential characteristics. The described embodiments are to be considered in all respects only as illustrative and not restrictive. The scope of the invention is, therefore. indicated by the appended claims rather than by the foregoing description. All changes which come within the meaning and range of equivalency of the claims are to be embraced within their scope.

What is claimed and desired to be secured by United States Letters Patent is:

1. A tooth whitening composition comprising:
   potassium nitrate included in an amount of at least about 0.1% by weight of the composition in order to reduce tooth sensitivity;
   a peroxide dental bleaching agent; and
   a carrier, wherein the tooth whitening composition is free of abrasives.

2. A tooth whitening composition as defined in claim 1, wherein the potassium nitrate is included in amount in range from about 1% to about 7% by weight of the tooth whitening composition.

3. A tooth whitening composition as defined in claim 1, wherein the carrier includes a tackifying agent.

4. A tooth whitening composition as defined in claim 3, wherein the tackifying agent is selected from the group consisting of carboxypolymethylene, gums, proteins, and mixtures thereof.

5. A tooth whitening composition as defined in claim 1, wherein the carrier includes water in an amount up to about 50% by weight of the tooth whitening composition.

6. A tooth whitening composition as defined in claim 1, wherein the carrier includes a polyol.

7. A tooth whitening composition as defined in claim 6, wherein the polyol is selected from the group consisting of glycerin, propylene glycol, polypropylene glycol, polyethylene glycol, sorbitol, and mixtures thereof.

8. A tooth whitening composition as defined in claim 1, further including at least one anticariogenic agent selected from the group consisting of chlorhexadine, tetracycline, cetl pyridinium chloride, benzalkonium chloride, cetyl pridinium bromide, methuyl benzoate, and proply benzoate.

9. A tooth whitening composition as defined in claim 1, further including at least one anticariogenic agent selected from the group consisting of sodium monofluorophosphate, sodium fluoride, and stannous fluoride.

10. A tooth whitening composition as defined in claim 1, wherein the dental bleaching agent is selected from the group consisting of hydrogen peroxide, carbamide peroxide, and mixtures thereof.

11. A tooth whitening composition as defined in claim 1, wherein the dental bleaching agent is included in an amount in a range from about 3% to about 20% by weight of the tooth whitening composition.

12. A tooth whitening composition as defined in claim 1, further including a bleaching agent stabilizer selected from the group consisting of EDTA, salts of EDTA, adipic acid, succinic acid, citric acid, and mixtures thereof.

13. A reduced sensitivity dental bleaching composition comprising:
   a peroxide dental bleaching agent;
   potassium nitrate included in an amount in order to reduce tooth sensitivity that may be caused by the dental bleaching agent; and
   a carrier, wherein the dental bleaching composition is free of abrasives.

14. A reduced sensitivity dental bleaching composition as defined in claim 13, wherein the dental bleaching agent is included in an amount in a range from about 3% to about 20% by weight of the dental bleaching composition and wherein the potassium nitrate is included in an amount in a range from about 0.1% to about 10% by weight of the dental bleaching composition.

15. A method for whitening teeth comprising:
   applying a tooth whitening composition to one or more of a person's teeth, the tooth whitening composition including:
      a peroxide dental bleaching agent;
      potassium nitrate included in an amount in order to reduce tooth sensitivity that may be caused by the dental bleaching agent; and
      a carrier, wherein the dental bleaching composition is free of abrasives; leaving the tooth whitening composition in passive contact with the one or more teeth for a desired period of time without brushing or scrubbing; and
   removing the tooth whitening composition after the desired period of time.

16. A method as defined in claim 15, wherein the potassium nitrate is included in an amount in a range from about 0.1% to about 10% by weight of the tooth whitening composition.

17. A method as defined in claim 15, wherein the dental bleaching agent is included in a range from about 3% to about 20% by weight of the tooth whitening composition.

18. A tooth whitening composition as defined in claim 3, wherein the tackifying agent is selected from the group consisting of polyacrylic copolymers, polyethylene oxides, and mixtures thereof.

19. A tooth whitening composition as defined in claim 6, wherein the polyol is selected from the group consisting of eryrthritol, mannitol, and mixtures thereof.

20. A tooth whitening composition as defined in claim 1, wherein the dental bleaching agent is selected from the group consisting of sodium perborate, benzoyl peroxide, glyceryl peroxide, and mixtures thereof.

21. A tooth whitening composition as defined in claim 1, further including a bleaching agent stabilizer selected from the group consisting of tin nitrate, tin phosphate, and mixtures thereof.

22. A method as defined in claim 15, wherein the tooth whitening composition is applied to the one or more teeth by means of a dental tray.

23. A method as defined in claim 22, wherein the dental tray is maintained in place over the one or more teeth for at least about one hour.

* * * * *

UNITED STATES PATENT AND TRADEMARK OFFICE
CERTIFICATE OF CORRECTION

PATENT NO. : 6,306,370 B1
DATED : October 23, 2001
INVENTOR(S) : Steven D. Jensen and Dan E. Fischer It is certified that error appears in the above-identified patent and that said Letters Patent is hereby corrected as shown below:

Column 1,
Line 52, "GCIY-OXIDE" to -- GLY-OXIDE --
Line 53, change "Canuick" to -- Carnrick --

Column 2,
Line 51, after "Alternatively" insert -- , --

Column 4,
Line 47, before "generally" delete "("
Line 53, change "prefelTed" to -- preferred --

Column 7,
Line 67, after "CARBOPOL" delete ","

Column 8,
Line 20, change "arc" to -- are --
Line 38, after "polyols" change "." to -- , --

Column 9,
Line 27, change "he" to -- the --

Column 11,
Line 66, change "vield" to -- yield --

Column 13,
Line 33, change "personas" to -- person's --
Line 56, change "Elowever" to -- However --

Column 14,
Line 12, after "19" change "." to -- , --
Line 47, after "CARBOPOL" delete ","
Line 50, after "mixture" change "." to -- , --

UNITED STATES PATENT AND TRADEMARK OFFICE
CERTIFICATE OF CORRECTION

PATENT NO.   : 6,306,370 B1
DATED        : October 23, 2001
INVENTOR(S)  : Steven D. Jensen and Dan E. Fischer It is certified that error appears in the above-identified patent and that said Letters Patent is hereby corrected as shown below:

Column 17,
Line 24, change "saccording" to -- according --

Column 20,
Line 13, change "anticariogenic" to -- antimicrobial --
Line 16, change "methuyl" to -- methyl --

Signed and Sealed this

Seventh Day of May, 2002

*Attest:*

JAMES E. ROGAN
*Attesting Officer*  *Director of the United States Patent and Trademark Office*